(12) United States Patent
Grizzard et al.

(10) Patent No.: US 10,932,841 B2
(45) Date of Patent: Mar. 2, 2021

(54) SPINAL IMPLANT SYSTEM AND METHOD

(71) Applicant: Warsaw Orthopedic, Inc., Warsaw, IN (US)

(72) Inventors: Mark R. Grizzard, Munford, TN (US); Julien Prevost, Memphis, TN (US); John A. Elliott, Atoka, TN (US); Michael C. Vincent, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 55 days.

(21) Appl. No.: 16/047,590

(22) Filed: Jul. 27, 2018

(65) Prior Publication Data

US 2020/0030015 A1    Jan. 30, 2020

(51) Int. Cl.
| | |
|---|---|
| *A61B 17/88* | (2006.01) |
| *A61B 17/70* | (2006.01) |
| *A61B 17/17* | (2006.01) |
| *A61B 17/16* | (2006.01) |

(52) U.S. Cl.
CPC ...... *A61B 17/8886* (2013.01); *A61B 17/1757* (2013.01); *A61B 17/7082* (2013.01); *A61B 17/1671* (2013.01)

(58) Field of Classification Search
CPC .............. A61B 17/7098; A61B 17/864; A61B 17/8802; A61B 17/8805; A61B 17/8841; A61B 17/8819; A61B 17/8825; A61B 17/8833; A61B 17/88–2017/8844
See application file for complete search history.

(56) References Cited

U.S. PATENT DOCUMENTS

| | | | | |
|---|---|---|---|---|
| 2,625,967 A | * | 1/1953 | Stull ....................... | B25B 23/10 81/57.42 |
| 3,312,127 A | * | 4/1967 | Stafford ................ | B23B 31/005 408/226 |
| 3,693,381 A | * | 9/1972 | McGee ................ | B25B 23/141 81/474 |
| 2009/0182345 A1 | * | 7/2009 | Medoff .............. | A61B 17/8019 606/105 |
| 2010/0114174 A1 | * | 5/2010 | Jones ................. | A61B 17/8816 606/279 |
| 2012/0059385 A1 | * | 3/2012 | Lewis ................ | A61B 17/8891 606/104 |

* cited by examiner

*Primary Examiner* — Zade Coley
(74) *Attorney, Agent, or Firm* — Sorell, Lenna & Scmidt, LLP

(57) ABSTRACT

A delivery system includes a first instrument having an outer sleeve defining a passageway. The first instrument includes an inner sleeve having a first end disposed in the passageway and a second end including a first mating element. The inner sleeve defines a channel. A second instrument includes a hollow shaft disposed in the channel and a handle coupled to the shaft. The handle includes a body and a second mating element extending from the body. The second mating element is configured to engage the first mating element to secure the second instrument to the first instrument. Methods are disclosed.

20 Claims, 18 Drawing Sheets

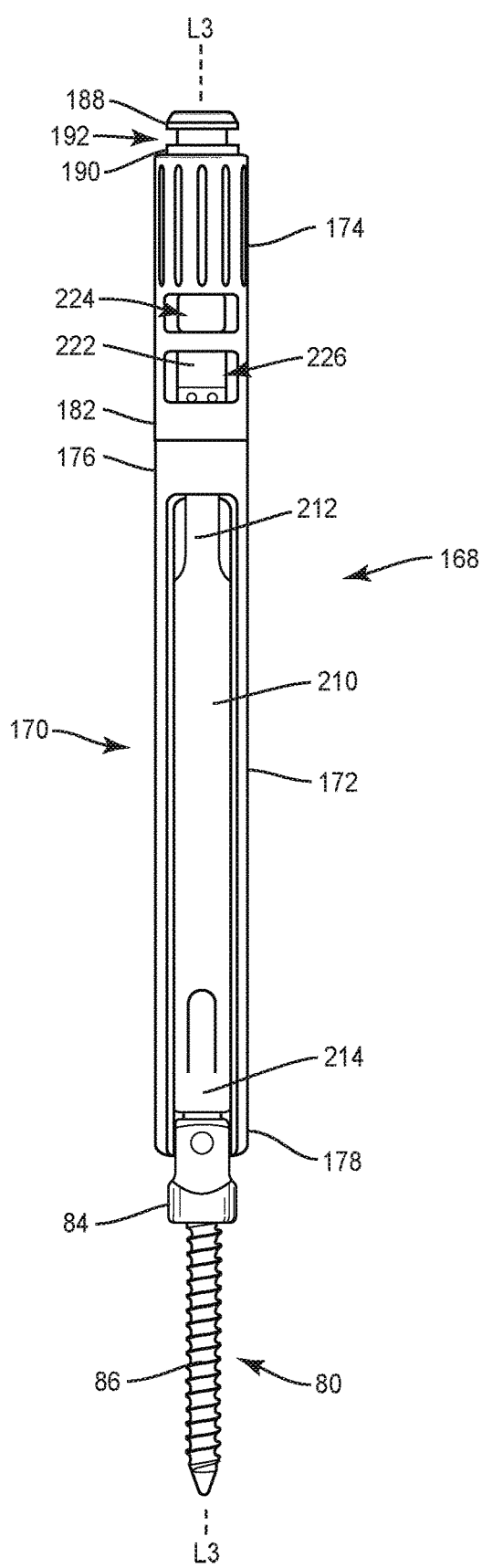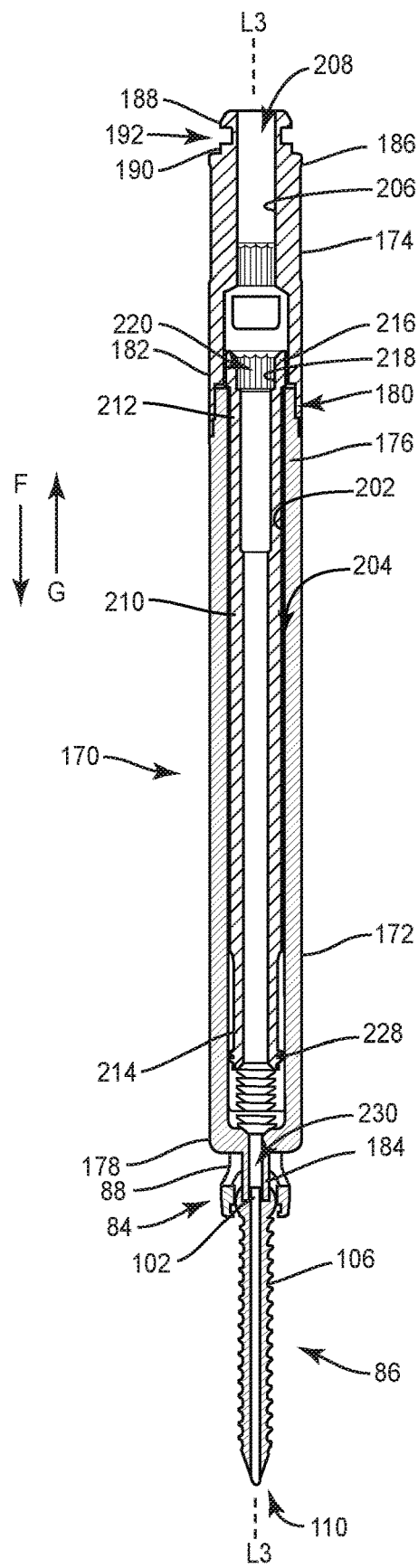
*FIG. 18*     *FIG. 19*

SPINAL IMPLANT SYSTEM AND METHOD

TECHNICAL FIELD

The present disclosure generally relates to medical devices for the treatment of musculoskeletal disorders, and more particularly to a spinal implant system and a method for treating a spine.

BACKGROUND

Spinal pathologies and disorders such as scoliosis, kyphosis, and other curvature abnormalities, degenerative disc disease, disc herniation, osteoporosis, spondylolisthesis, stenosis, tumor and fracture may result from factors including trauma, disease and degenerative conditions caused by injury and aging. Spinal disorders typically result in symptoms including deformity, pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes correction, fusion, fixation, discectomy, laminectomy and implantable prosthetics. As part of these surgical treatments, spinal constructs such as vertebral rods are often used to provide stability to a treated region. Rods redirect stresses away from a damaged or defective region while healing takes place to restore proper alignment and generally support vertebral members. During surgical treatment, one or more rods and bone fasteners can be delivered to a surgical site. The rods may be attached via the bone fasteners to the exterior of two or more vertebral members. A surgeon may stabilize the vertebra by using a driver to insert the bone fasteners into the damaged vertebral body and attach the fasteners to one or more rods to help support and stabilize the damaged vertebra. It is sometimes difficult for the surgeon to achieve the required support and stabilization for the damaged vertebral body because the threads of the bone fasteners do not properly engage the vertebral bone. Therefore, the surgeon may insert a bone filler device into the driver to deliver an adhesive material or cement material in and/or around at least one of the bone fasteners using an injection gun that is coupled to the bone filler device to further bond at least one of the fasteners with bone. However, the injection gun often generates back pressure that causes the bone filler device to become disconnected from the driver. As a result, a separate instrument is required to prevent the bone filler device from being disconnected from the driver when the injection gun generates back pressure. Another common method of cement injection uses one hand to hold the bone filler device in place, which acts as resistance to back pressure. A plunger is used by the other hand to distribute the cement. This disclosure describes an improvement over these prior technologies.

SUMMARY

In one embodiment, a delivery system is provided. The delivery system comprises a first instrument and a second instrument. The first instrument comprises an outer sleeve defining a passageway. The first instrument comprises an inner sleeve having a first end disposed in the passageway and a second end that includes a first mating element. The inner sleeve defines a channel. The second instrument comprises a hollow shaft that is disposed in the channel and a handle that is coupled to the shaft. The handle comprises a body and a second mating element that extends from the body. The second mating element is configured to engage the first mating element to secure the second instrument to the first instrument. In some embodiments, methods are disclosed.

In one embodiment, a delivery system is provided. The delivery system comprises an implant, a first instrument and a second instrument. The implant comprises a threaded screw and a head that is coupled to the screw. The screw comprises a bore that extends through opposite ends of the screw. The head has a threaded inner surface. The first instrument comprises an outer sleeve defining a passageway. The first instrument comprises an inner sleeve having a first end that is rotatably disposed in the passageway and a second end that includes a first mating element. The first end comprises a threaded outer surface that engages the threaded inner surface to couple the inner sleeve to the head. The first end comprises a tip that is positioned in the bore to couple the inner sleeve to the screw. The inner sleeve defines a channel. The second instrument comprises a hollow shaft that is disposed in the channel and a handle that is coupled to the shaft. The handle comprises a body and a second mating element that extends from the body. The second mating element engages the first mating element to secure the second instrument to the first instrument such that the second instrument is prevented from translating proximally relative to the first instrument.

In one embodiment, a delivery system is provided. The delivery system comprises a bone fastener, a driver, a bone filler device and an injector. The bone fastener comprises a threaded screw and a head that is coupled to the screw. The screw is rotatable relative to the head in multiple planes. The screw comprises an inner surface defining a bore that extends through opposite ends of the screw. The screw comprises an opening that extends through the inner surface and an opposite outer surface of the screw. The head has a threaded inner surface. The driver comprises an outer sleeve defining a passageway. The driver comprises an inner sleeve having a first end that is rotatably disposed in the passageway and a second end that includes a flange. The first end comprises a threaded outer surface that engages the threaded inner surface to couple the inner sleeve to the head. The first end comprises a tip that is positioned in the bore to couple the inner sleeve to the screw. The inner sleeve defines a channel. The bone filler device comprises a hollow shaft that is disposed in the channel and a handle that is coupled to the shaft. The handle comprises a body including a cylindrical portion that is coaxial with the shaft. The cylindrical portion has a threaded outer surface and an inner surface defining an opening that is in communication and coaxial with a lumen of the shaft. The handle comprises a first wing that extends from a first side the body in a cantilevered configuration and a second wing that extends from an opposite second side of the body in a cantilevered configuration. The first wing comprises an extension that extends from the first side and a tab that extends from the extension. The second wing comprises an extension that extends from the second side and a tab that extends from the extension of the second wing. The extensions each extend parallel to a longitudinal axis defined by the shaft and the tabs each extend perpendicular to the longitudinal axis. The tabs engage the flange to secure the bone filler device to the driver such that the bone filler device is prevented from translating proximally relative to the driver. The injector is coupled to the handle and comprises bone cement therein. The injector is configured to deliver the bone cement through the channel and into the bore.

BRIEF DESCRIPTION OF THE DRAWINGS

The present disclosure will become more readily apparent from the specific description accompanied by the following drawings, in which:

FIG. 18 is a side view of one embodiment of a component of the surgical system shown in FIG. 17 in accordance with the principles of the present disclosure;

FIG. 19 is a side, cross sectional view of the component shown in FIG. 18;

DETAILED DESCRIPTION

Figure 1:
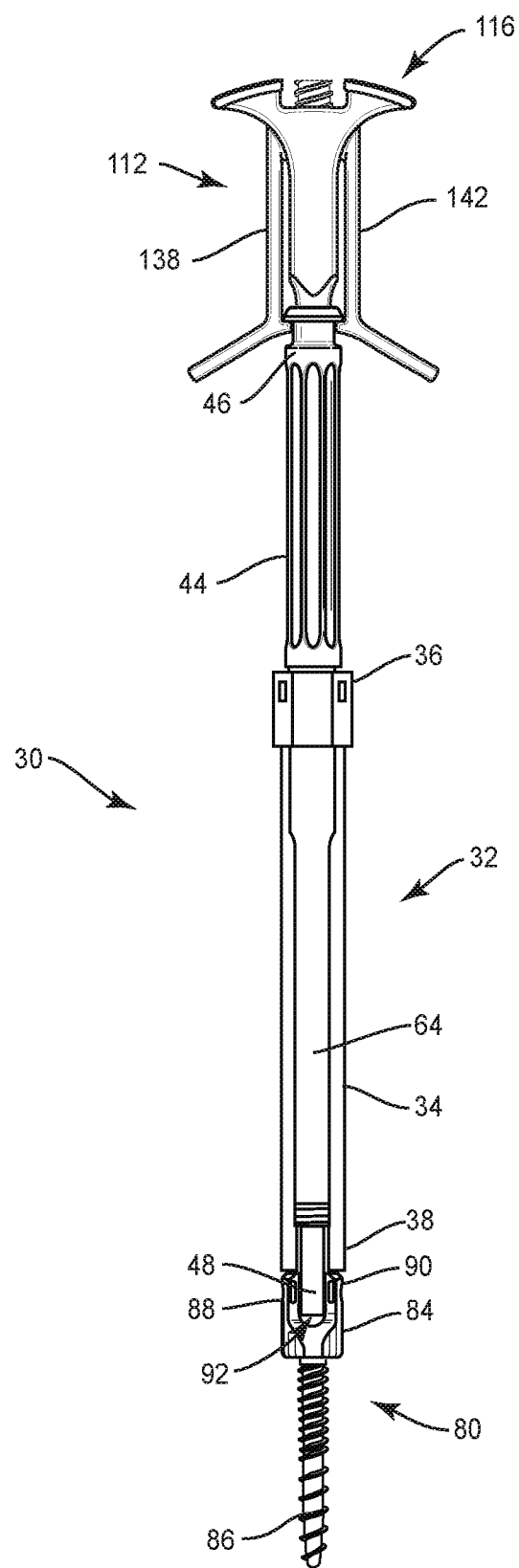
FIG. 1 is a side view of components of one embodiment of a surgical system in accordance with the principles of the present disclosure.
Figure 2:
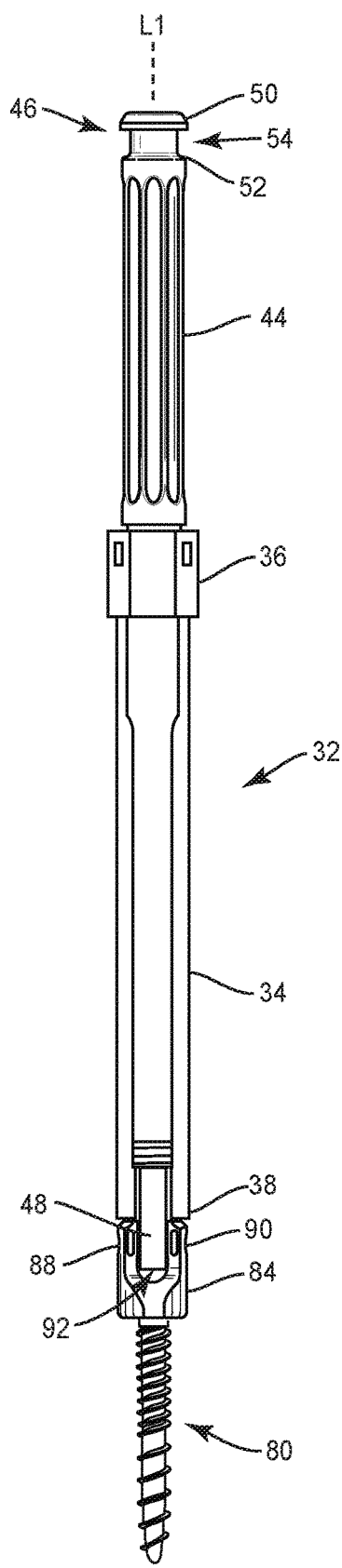
FIG. 2 is a side view of one embodiment of a component of the surgical system shown in FIG. 1 in accordance with the principles of the present disclosure.

The exemplary embodiments of the surgical system and related methods of use disclosed are discussed in terms of medical devices for the treatment of musculoskeletal disorders and more particularly, in terms of a delivery system and a method for treating a spine. In some embodiments, the systems and methods of the present disclosure comprise medical devices including surgical instruments and implants that are employed with a surgical treatment, as described herein, for example, with a cervical, thoracic, lumbar and/or sacral region of a spine.

A cement delivery gun creates back pressure when used in connection with a predicate bone filler device. A current fenestrated screw system relies on an extra instrument to counteract the back pressure generated by the cement delivery system gun. On the other hand, in various embodiments, the delivery system of the present disclosure simplifies the procedure by removing unnecessary steps while still providing the function needed. In some embodiments, the present delivery system eliminates the need for a separate instrument to secure a bone filler device to its guide/driver and includes a handle having a specific shape developed to retain proper connection between the handle and the guide/driver during cement application. In some embodiments, the handle includes wings having a shape that allows both easy attachment to an undercut in the guide/driver. The handle also provides an ergonomic feature that allows simple release the bone filler device from the guide/driver. In some embodiments, a distal end of the handle having a conical shape that helps facilitate axilization of the bone filler device ensuring proper assembly of the handle with the guide/driver by aligning the handle with the guide/driver. In some embodiments, the handle and/or guide/drive will create clicking during assembly of the handle with the guide/driver to indicate that the handle has been properly assembled with the guide/driver.

In some embodiments, the delivery system of the present disclosure may be employed to treat spinal disorders such as, for example, degenerative disc disease, disc herniation, osteoporosis, spondylolisthesis, stenosis, scoliosis, kyphosis, and other curvature abnormalities, tumor and fractures. In some embodiments, the delivery system of the present disclosure may be employed with other osteal and bone related applications, including those associated with diagnostics and therapeutics. In some embodiments, the disclosed delivery system may be alternatively employed in a surgical treatment with a patient in a prone or supine position, and/or employ various surgical approaches to the spine, including anterior, posterior, posterior mid-line, direct lateral, postero-lateral, and/or antero-lateral approaches, and in other body regions. The delivery system of the present disclosure may also be alternatively employed with procedures for treating the lumbar, cervical, thoracic, sacral and pelvic regions of a spinal column. The delivery system of the present disclosure may also be used on animals, bone models and other non-living substrates, such as, for example, in training, testing and demonstration.

The delivery system of the present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. In some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about"

or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

As used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, microdiscectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. In some embodiments, as used in the specification and including the appended claims, the term "tissue" includes soft tissue, ligaments, tendons, cartilage and/or bone unless specifically referred to otherwise.

The following discussion includes a description of a delivery system and related components and methods of employing the delivery system in accordance with the principles of the present disclosure. Alternate embodiments are also disclosed. Reference is made in detail to the exemplary embodiments of the present disclosure, which are illustrated in the accompanying figures. Turning to FIGS. 1-21, there are illustrated components of a delivery system, such as, for example, a delivery system 30.

The components of delivery system 30 can be fabricated from biologically acceptable materials suitable for medical applications, including metals, synthetic polymers, ceramics and bone material and/or their composites. For example, the components of delivery system 30, individually or collectively, can be fabricated from materials such as stainless steel alloys, aluminum, commercially pure titanium, titanium alloys, Grade 5 titanium, super-elastic titanium alloys, cobalt-chrome alloys, superelastic metallic alloys (e.g., Nitinol, super elasto-plastic metals, such as GUM METAL®), ceramics and composites thereof such as calcium phosphate (e.g., SKELITE™), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations.

Various components of delivery system 30 may have material composites, including the above materials, to achieve various desired characteristics such as strength, rigidity, elasticity, compliance, biomechanical performance, durability and radiolucency or imaging preference. The components of delivery system 30, individually or collectively, may also be fabricated from a heterogeneous material such as a combination of two or more of the above-described materials. The components of delivery system 30 may be monolithically formed, integrally connected or include fastening elements and/or instruments, as described herein.

Delivery system 30 is employed, for example, with a fully open surgical procedure, a minimally invasive procedure including percutaneous techniques, and mini-open surgical techniques to deliver and introduce instrumentation and/or a spinal implant, such as, for example, a bone fastener, at a surgical site of a patient, which includes, for example, a spine. In some embodiments, the spinal implant can include one or more components of one or more spinal constructs, such as, for example, interbody devices, interbody cages, bone fasteners, spinal rods, tethers, connectors, plates and/or bone graft, and can be employed with various surgical procedures including surgical treatment of a cervical, thoracic, lumbar and/or sacral region of a spine.

Figure 3:
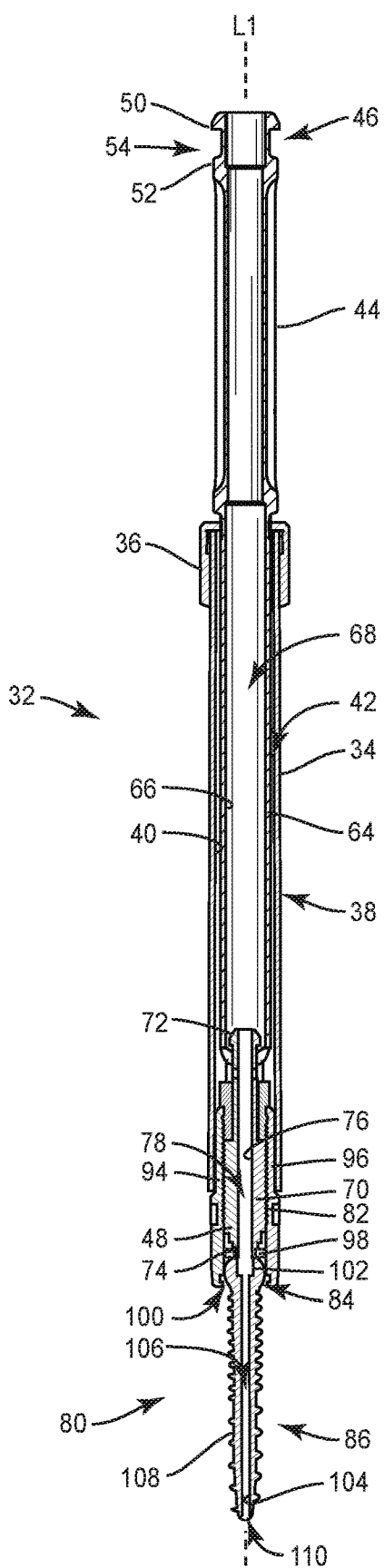
FIG. 3 is a side, cross sectional view the component shown in FIG. 2.

Delivery system 30 includes a first instrument, such as, for example, a driver 32. Driver 32 includes a sleeve, such as, for example, an outer sleeve 34 that extends along a longitudinal axis L1 between an end 36 and an opposite end 38. Sleeve 34 has an inner surface 40 defining a passageway 42, as best shown in FIG. 3. Passageway 42 is coaxial with axis L1 and extends the entire length of sleeve 34 such that passageway 42 extends through opposite end surfaces of ends 36, 38. In some embodiments, passageway 42 has a circular diameter. In some embodiments, passageway 42 has a uniform diameter along the entire length of passageway 42. In some embodiments, passageway 42 may be disposed at alternate orientations, relative to axis L1, such as, for example, transverse, perpendicular and/or other angular orientations such as acute or obtuse, co-axial and/or may be offset or staggered. In some embodiments, passageway 42 may have various cross section configurations, such as, for example, oval, oblong, triangular, rectangular, square, polygonal, irregular, uniform, non-uniform, variable, tubular and/or tapered.

Figure 4:
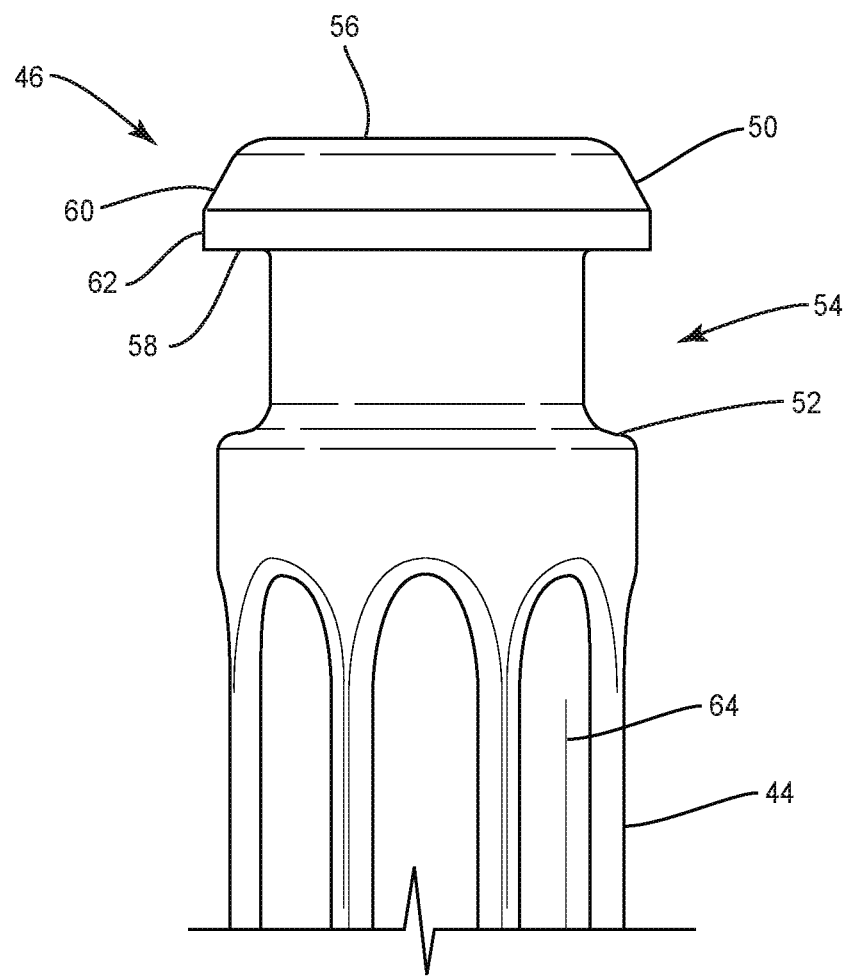
FIG. 4 is an enlarged side view of a portion of the component shown in FIG. 2.
Figure 5:
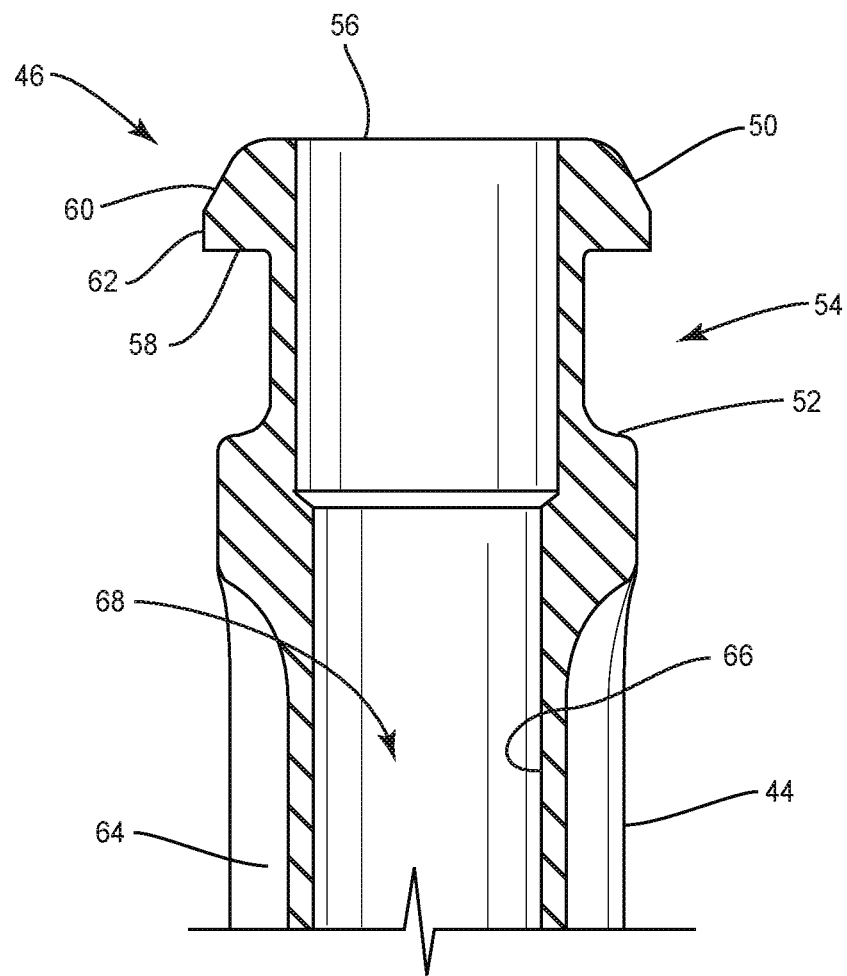
FIG. 5 is an enlarged, cross sectional side view of a portion of the component shown in FIG. 2.
Figure 6:
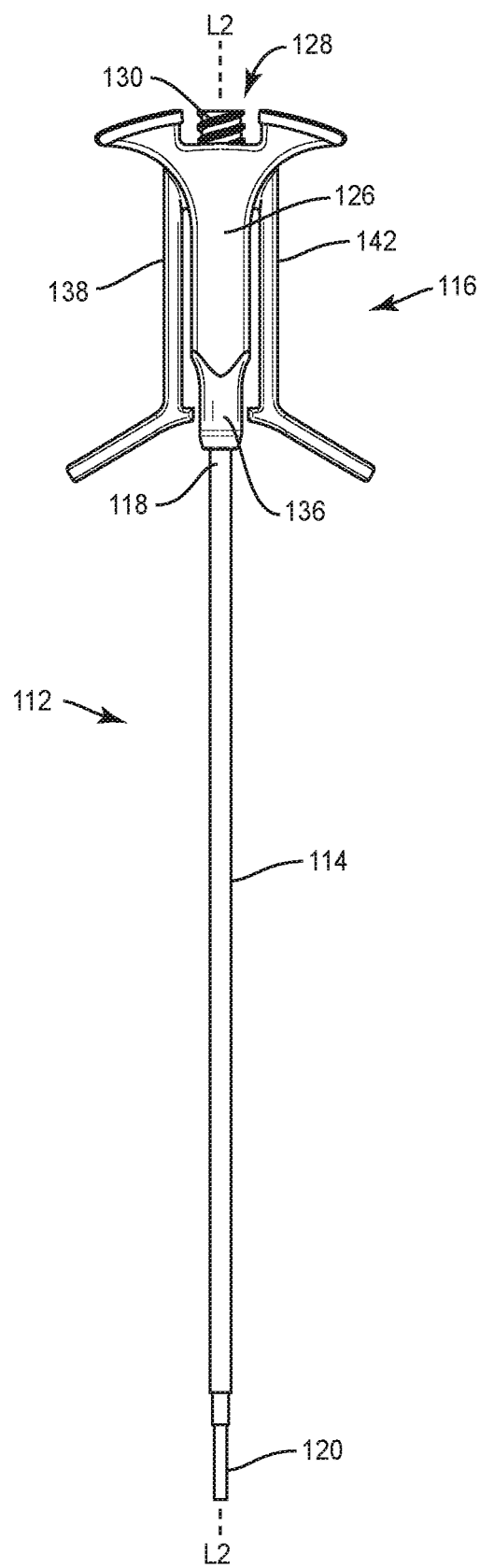
FIG. 6 is a side view of one embodiment of a component of the surgical system shown in FIG. 1 in accordance with the principles of the present disclosure.

Driver 32 includes a sleeve, such as, for example, an inner sleeve 44 rotatably disposed in passageway 42 such that sleeve 44 is coaxial with axis L1. Sleeve 44 extends between an end 46 and an opposite end 48 that is disposed in passageway 42. End 46 includes a first mating element, such as, for example, a flange 50 that is spaced apart from a flange 52 by an undercut, such as, for example, a recess 54. Flange 50 includes opposite surfaces 56, 58 that each extend perpendicular to axis L1 and surfaces 60, 62 that are each positioned between surfaces 56, 58, as best shown in FIGS. 4 and 5. Surface 56 defines the end surface of end 46. Surface 60 extends transverse to axis L1 and surface 62 extends parallel to axis L1.

Sleeve 44 includes a body 64 having an inner surface 66 that defines a channel 68, as best shown in FIG. 3. Channel 68 is coaxial with axis L1 and extends the entire length of sleeve 44 such that channel 68 extends through surface 56 and an opposite end surface of end 48. In some embodiments, channel 68 has a circular diameter. In some embodiments, channel 68 has a uniform diameter along the entire length of channel 68. In some embodiments, channel 68 may be disposed at alternate orientations, relative to axis L1, such as, for example, transverse, perpendicular and/or other angular orientations such as acute or obtuse, co-axial and/or may be offset or staggered. In some embodiments, channel 68 may have various cross section configurations, such as, for example, oval, oblong, triangular, rectangular, square, polygonal, irregular, uniform, non-uniform, variable, tubular and/or tapered.

End 48 includes a tip 70 that is connected with body 64, as best shown in FIG. 3. In some embodiments, tip 70 is removably connected with body 64 such that tip 70 is disposable. In such embodiments, tip 70 may be provisionally fixed with body 64 such that rotation of body 64 also rotates tip 70. In some embodiments, tip 70 is variously connected with body 64, such as, for example, frictional engagement, threaded engagement, mutual grooves, screws, adhesive, nails, barbs and/or raised element. In some embodiments, tip 70 is integrally and/or monolithically formed with body 64 such that tip 70 cannot be removed from body 64 without breaking body 64 and/or tip 70. Tip 70 extends between an end 72 and an opposite end 74. Tip 70 includes an inner surface 76 defining a bore 78 that is coaxial with axis L1 and extends the entire length of tip 70 such that bore 78 extends through opposite end surfaces of ends 72, 74. In some embodiments, bore 78 has a circular diameter. In some embodiments, bore 78 has a uniform diameter along the entire length of bore 78. In some embodiments, bore 78 may be disposed at alternate orientations, relative to axis L1, such as, for example, transverse, perpendicular and/or other angular orientations such as acute or obtuse, co-axial and/or may be offset or staggered. In some embodiments, bore 78 may have various cross section configurations, such as, for example, oval, oblong, triangular, rectangular, square, polygonal, irregular, uniform, non-uniform, variable, tubular and/or tapered. End 72 is positioned in channel 68 such that bore 78 is in communication and coaxial with channel 68. End 74 defines a drive portion configured for engagement with an implant, such as, for example, a bone fastener 80, as discussed herein. In some embodiments, the drive portion may include a square, triangular, polygonal, star or hexalobe cross sectional configuration configured engage a correspondingly shaped portion of fastener 80. In some embodiments, tip 70 includes a threaded outer surface that is configured to engage threads of fastener 80 to couple sleeve 44 to fastener 80, as discussed herein.

Fastener 80 includes a head, such as, for example, an implant receiver 84 and a screw shaft 86 that is coupled to receiver 84. Implant receiver 84 extends parallel to axis L1 when fastener 80 is coupled to sleeve 44. Implant receiver 84 includes a pair of spaced apart arms 88, 90 that define an implant cavity 92 therebetween configured for disposal of a spinal construct, such as, for example, a spinal rod. Arms 88, 90 each extend parallel to axis L1 when fastener 80 is coupled to sleeve 44. In some embodiments, arm 88 and/or arm 90 may be disposed at alternate orientations, relative to axis L1, such as, for example, transverse, perpendicular and/or other angular orientations such as acute or obtuse, coaxial and/or may be offset or staggered. Arms 88, 90 each include an arcuate outer surface extending between a pair of side surfaces. At least one of the outer surfaces and the side surfaces of arms 88, 90 have at least one recess or cavity therein configured to receive an insertion tool, compression instrument and/or instruments for inserting and tensioning bone fastener 80.

Arm 88 includes a break away tab 94 that is frangibly connected to arm 88 (FIG. 3) such that manipulation of tab 94 relative to arm 88 can fracture and separate tab 94 from arm 88 at a predetermined force and/or torque limit, as described herein. In some embodiments, as force and/or torque is applied to tab 94 and resistance increases, for example, the predetermined torque and force limit is approached. Arm 90 includes a break away tab 96 that is frangibly connected to arm 90 such that manipulation of tab 96 relative to arm 90 can fracture and separate tab 96 from arm 90 at a predetermined force and/or torque limit, as described herein. In some embodiments, as force and/or torque is applied to tab 96 and resistance increases, for example, the predetermined torque and force limit is approached.

In some embodiments, tabs 94, 96 can fracture and separate at a predetermined force or torque limit, which may be in a range of approximately 2 Newton meters (N-m) to 8 Nm. In some embodiments, tabs 94, 96 and arms 88, 90 may have the same or alternate cross section configurations, may be fabricated from a homogenous material or heterogeneously fabricated from different materials, and/or alternately formed of a material having a greater degree, characteristic or attribute of plastic deformability, frangible property and/or break away quality to facilitate fracture and separation of tabs 94, 96 from arms 88, 90.

Cavity 92 is substantially U-shaped. In some embodiments, all or only a portion of cavity 92 may have alternate cross section configurations, such as, for example, closed, V-shaped, W-shaped, oval, oblong triangular, square, polygonal, irregular, uniform, non-uniform, offset, staggered, and/or tapered. Implant receiver 84 includes thread forms configured for engagement with a coupling member, such as, for example, a setscrew to retain a spinal rod within cavity 92. The thread forms of implant receiver 84 may also engage threaded outer surface 82 of tip 70 to couple sleeve 44 to implant receiver 84, as discussed herein. In some embodiments, the inner surface of implant receiver 84 may be disposed with the coupling member and/or tip 70 in alternate fixation configurations, such as, for example, friction fit, pressure fit, locking protrusion/recess, locking keyway and/or adhesive. In some embodiments, all or only a portion of the inner surface of implant receiver 84 may have alternate surface configurations to enhance engagement with a spinal rod, a setscrew and/or tip 70, such as, for example, rough, arcuate, undulating, mesh, porous, semi-porous, dimpled and/or textured. In some embodiments, implant receiver 92 may include alternate configurations, such as, for example, closed, open and/or side access. In some embodiments, bone fastener 80 includes a crown 98 configured to facilitate positioning of a spinal rod.

Implant receiver 84 defines a cavity 100 configured for disposal of a head of screw shaft 86, as described herein.

Screw shaft 86 includes a socket, such as, for example, a tool engaging portion 102 configured to engage the drive portion of end 74. Screw shaft 86 includes an outer surface having an external thread form. In some embodiments, the external thread form may include a single thread turn or a plurality of discrete threads. Screw shaft 86 includes an inner surface 104 defining a bore 106 that extends the entire length of screw shaft 86. When the drive portion of end 74 engages tool engaging portion 102, bore 78 is in communication and coaxial with bore 106. In some embodiments, screw shaft 86 includes one or a plurality of openings that each extend through surface 104 and an opposite outer surface 108 of screw shaft 86 such that a material, such as, for example, bone cement disposed in bore 106 can exit bore 106 through one of the openings that extend through surfaces 104, 108 and/or through an opening 110 in a distal end of screw shaft 86 that is coaxial with axis L1 when fastener 80 is coupled to sleeve 44.

In some embodiments, implant receiver 84 is manually engageable with screw shaft 86 in a non-instrumented assembly, as described herein. In some embodiments, manual engagement and/or non-instrumented assembly of implant receiver 84 and screw shaft 86 includes coupling without use of separate and/or independent instrumentation engaged with the components to effect assembly. In some embodiments, manual engagement and/or non-instrumented assembly includes a practitioner, surgeon and/or medical staff grasping implant receiver 84 and screw shaft 86 and forcibly assembling the components. In some embodiments, manual engagement and/or non-instrumented assembly includes a practitioner, surgeon and/or medical staff grasping implant receiver 84 and screw shaft 86 and forcibly snap fitting the components together, as described herein. In some embodiments, manual engagement and/or non-instrumented assembly includes a practitioner, surgeon and/or medical staff grasping implant receiver 84 and screw shaft 86 and forcibly pop fitting the components together and/or pop fitting implant receiver 84 onto screw shaft 86, as described herein. In some embodiments, a force in a range of 2-50 N is required to manually engage implant receiver 84 and screw shaft 86 and forcibly assemble the components. In some embodiments, a force in a range of 5-10 N is required to manually engage implant receiver 84 and screw shaft 86 and forcibly assemble the components.

In some embodiments, implant receiver 84 is connectable with screw shaft 86 such that screw shaft 86 is pivotable and/or rotatable relative to implant receiver 84 in a plurality of planes. In some embodiments, implant receiver 84 is connectable with screw shaft 86 to include various configurations, such as, for example, a posted screw, a pedicle screw, a bolt, a bone screw for a lateral plate, an interbody screw, a uni-axial screw (UAS), a fixed angle screw (FAS), a multi-axial screw (MAS), a side loading screw, a sagittal adjusting screw (SAS), a transverse sagittal adjusting screw (TSAS), an awl tip (ATS), a dual rod multi-axial screw (DRMAS), midline lumbar fusion screw and/or a sacral bone screw.

To connect driver 32 with fastener 80, tip 70 is inserted into implant cavity 92 and sleeve 44 is rotated relative to sleeve 34 such that the threads on outer surface 82 of tip 70 mate with the thread forms of implant receiver 84 to couple sleeve 44 with receiver 84. Sleeve 44 is further rotated relative to sleeve 34 such that the drive portion of end 74 is positioned in tool engaging portion 102 to couple sleeve 44 with screw 86. In some embodiments, the threads on outer surface 82 of tip 70 mate with the thread forms of implant receiver 84 at the same time that the drive portion of end 74 is positioned in tool engaging portion 86 to position receiver 84 relative to screw 86 such that receiver 84 and screw 86 extend parallel to axis L1 and maintain such positioning as fastener 80 is driven into bone or other tissue using driver 32, as discussed herein. That is, mating the threads on outer surface 82 of tip 70 with the thread forms of implant receiver 84 at the same time that the drive portion of end 74 is positioned in tool engaging portion 86 prevents receiver 84 from pivoting relative to screw 86.

Delivery system 30 includes a second instrument, such as, for example, a bone filler device 112. Device 112 includes a shaft 114 and a handle 116 that is coupled to shaft 114. In some embodiments, handle 116 is permanently fixed to shaft 114 such that handle 116 cannot be removed from shaft 114 without breaking handle 116 and/or shaft 114. In some embodiments, handle 116 is integrally and/or monolithically formed with shaft 114. In some embodiments, handle 116 is removably connected with shaft 114 such that handle 116 can be removed from shaft 114 without breaking handle 116 and/or shaft 114.

Figure 7:
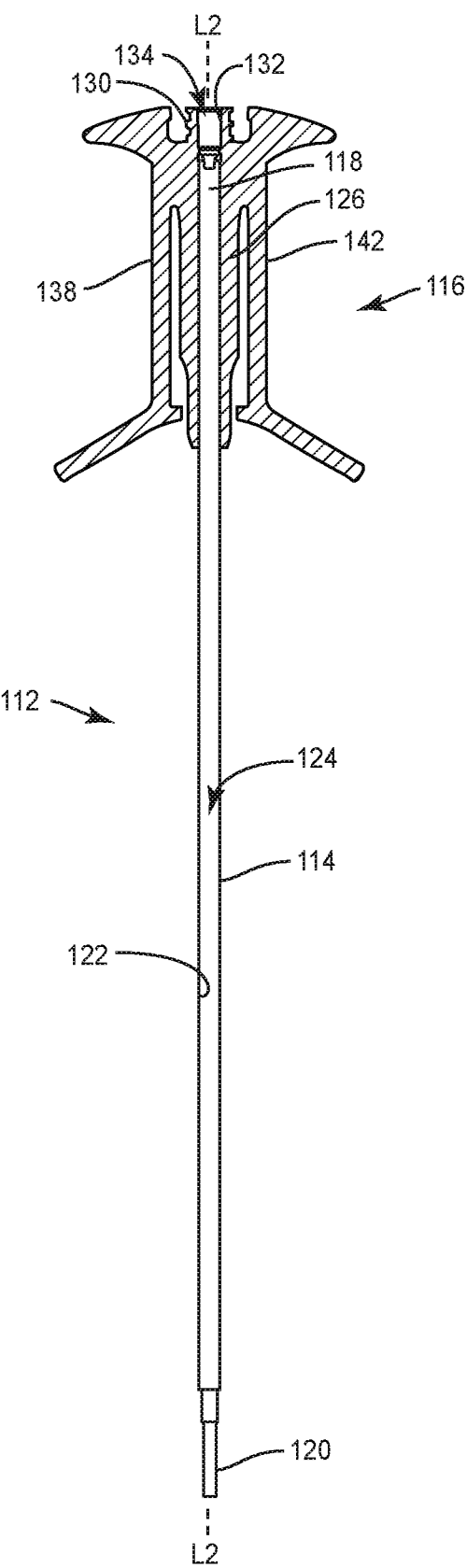
FIG. 7 is a side, cross sectional view of the component shown in FIG. 6.

Shaft 114 is configured for disposal in channel 68 and extends along a longitudinal axis L2 between an end 118 and an opposite end 120. Handle 116 is connected with end 118. In some embodiments, shaft 114 is tapered from end 118 to end 120 such that end 118 has a minimum diameter that is greater than a minimum diameter of end 120. In some embodiments, shaft 114 has a uniform diameter along the entire length of shaft 114. Shaft 114 comprises an inner surface 122 that defines a lumen 124, as best shown in FIG. 7. Lumen 124 is coaxial with axis L2 and extends the entire length of shaft 114 such that lumen 124 extends through opposite end surfaces of ends 118, 120. In some embodiments, lumen 124 has a circular diameter. In some embodiments, lumen 124 has a diameter that tapers along the length of shaft 114. In some embodiments, lumen 124 may be disposed at alternate orientations, relative to axis L2, such as, for example, transverse, perpendicular and/or other angular orientations such as acute or obtuse, co-axial and/or may be offset or staggered. In some embodiments, lumen 124 may have various cross section configurations, such as, for example, oval, oblong, triangular, rectangular, square, polygonal, irregular, uniform, non-uniform, variable, tubular and/or tapered.

Handle 116 comprises a body 126 including a cylindrical portion 128 that is coaxial with shaft 114 and axis L2. Cylindrical portion 128 has a threaded outer surface 130 and an opposite inner surface 132 defining an opening 134 that is in communication and coaxial with lumen 124, as best shown in FIG. 7. Body 126 comprises a conical portion 136 opposite cylindrical portion 128. Conical portion 136 is configured for disposal in channel 68 to connect handle 116 with sleeve 44, as discussed herein. Conical portion 136 helps facilitate axialization of device 112 relative to driver 32 to ensure proper assembly.

Handle 116 comprises a second mating element that includes a first wing 138 that extends from a first side 140 of body 126 in a cantilevered configuration and a second wing 142 that extends from an opposite second side 144 of body 126 in a cantilevered configuration. Wing 138 comprises an extension 146 that extends from first side 140, a gripping portion 148 that extends from extension 146 and a tab 150 that extends from extension 146. Wing 142 comprises an extension 152 that extends from second side 144, a gripping portion 154 that extends from extension 152 and a tab 156 that extends from extension 152. Extensions 146,152 each extend parallel to axis L2. Gripping portions 148, 154 each extend transverse to axis L2. Tabs 150, 156 each extend perpendicular to axis L2. Tab 150 includes a surface 150a that extends parallel to axis L2 and tab 156 includes a surface 156a that extends parallel to axis L2. Surface 150a faces surface 156a. Tab 150 includes a surface 150b that extends perpendicular to axis L2 and tab 156 includes a surface 156b that extends perpendicular to axis L2. Tabs 150, 156 are configured to engage flange 50 to secure the device 112 to driver 32 such that device 112 is prevented from translating axially relative to driver 32 in the direction shown by arrow A in FIG. 12. Surface 150a is spaced a first distance apart from surface 156a when no forces are applied to wings 138, 142. Wings 138, 142 are configured to deflect relative to body 126. For example, a force may be applied to gripping portion 148 to move gripping portion 148 relative to body 126 in the direction shown by arrow B in FIG. 8 and a force may be applied to gripping portion 154 to move gripping portion 154 relative to body 126 in the direction shown by arrow C in FIG. 8 such that tabs 150, 156 move away from one another and surface 150a is spaced an increased second distance apart from surface 156a. In some embodiments, wings 138, 142 are resiliently biased inwardly such that after the forces are removed from gripping portions 148, 154 tabs 150, 156 move toward one another such that surface 150a is spaced the first distance apart from surface 156a.

Figure 11:
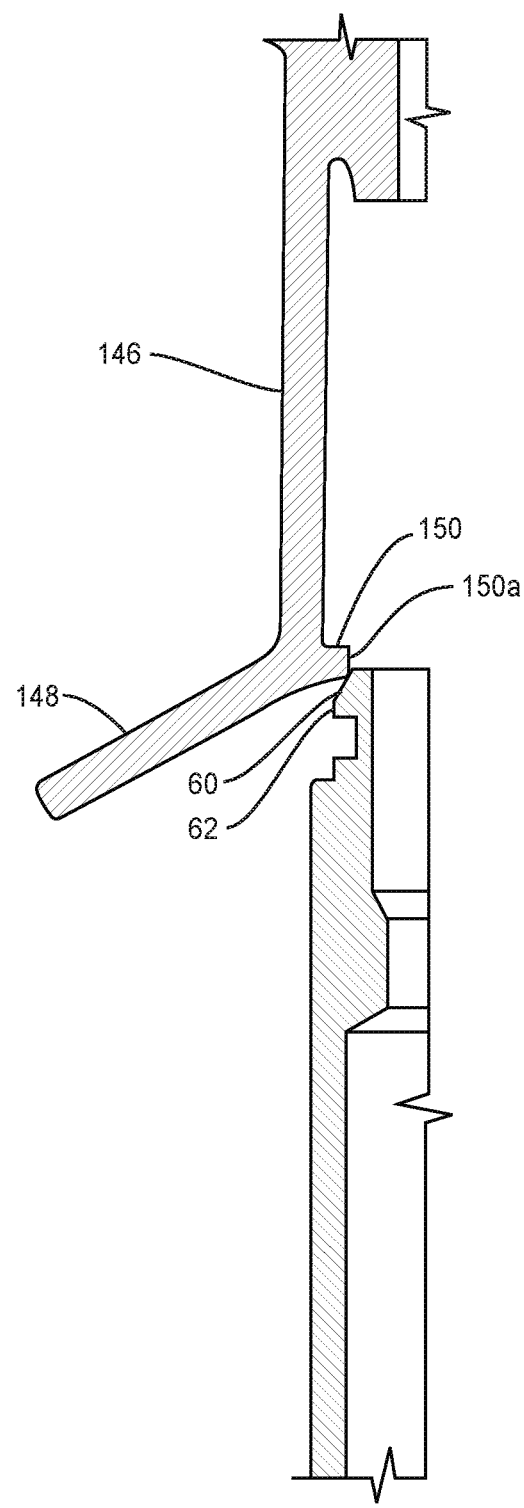
FIG. 11 is an enlarged, cross sectional side view of a portion of the surgical system shown in FIG. 1, with the components in an unassembled configuration.
Figure 12:
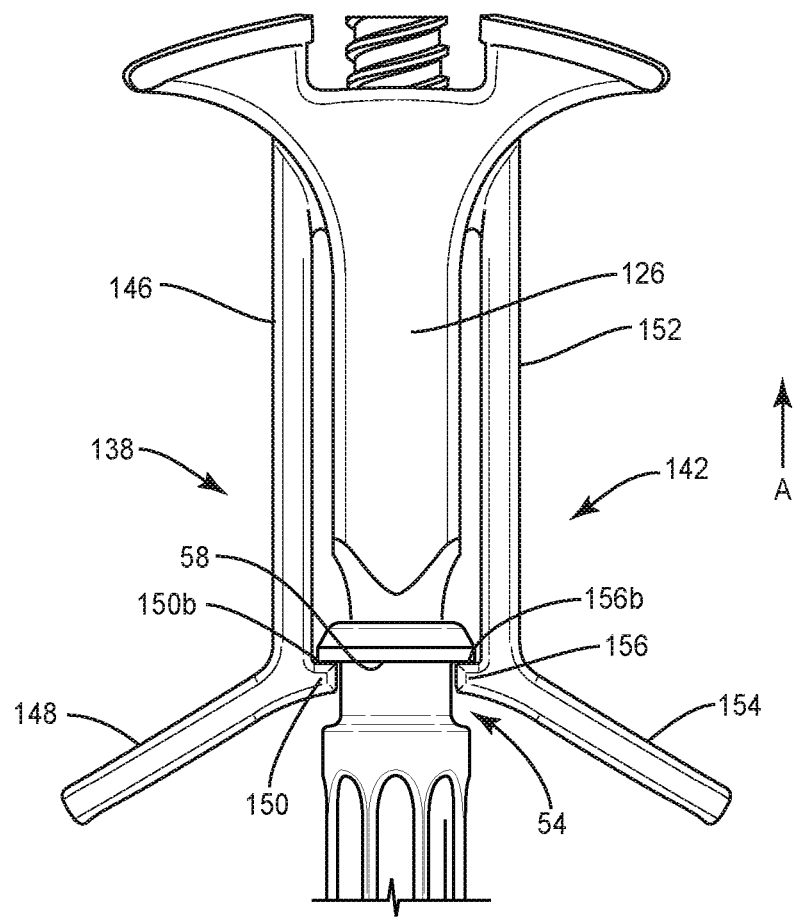
FIG. 12 is an enlarged side view of a portion of components of the surgical system shown in FIG. 1, with the components in an assembled configuration.
Figure 13:
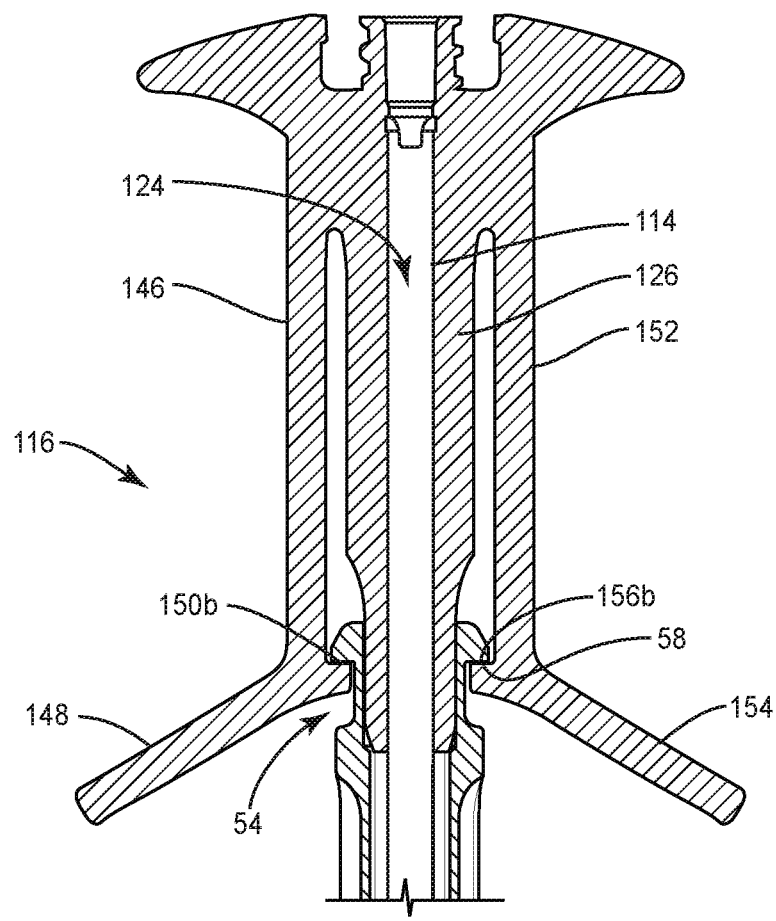
FIG. 13 is an enlarged, cross sectional side view of a portion of components of the surgical system shown in FIG. 1, with the components in an assembled configuration.

To connect device 112 with sleeve 44, shaft 114 is inserted into channel 68 such that axis L2 is coaxial with axis L1. Device 112 is then translated axially relative to sleeve 44 in the direction shown by arrow D in FIG. 9 until conical portion 136 is positioned within channel 68. As device 112 translates axially relative to sleeve 44 in the direction shown by arrow D in FIG. 9, surface 150a of tab 150 slides along surface 60 of flange 50, as shown in FIG. 11 and surface 156a of tab 156 slides along surface 60. As surfaces 150a, 156a slide along surface 60, wings 138, 142 deflect outwardly from body 126 such that the distance between surfaces 150a, 156a increase from the first distance to a second distance. Device 112 is further translated axially relative to sleeve 44 in the direction shown by arrow D in FIG. 9 when surfaces 150a, 156a are spaced apart by the second distance such that surfaces 150a, 156a slide along surface 62 of flange 50. Device 112 is further translated axially relative to sleeve 44 in the direction shown by arrow D in FIG. 9 such that tabs 150, 156 are aligned with recess 54. The inward bias of wings 138, 142 causes tabs 150, 156 to move toward one another such that surface 150a is spaced the first distance apart from surface 156a and surfaces 150b, 156b engage surface 58 of flange 50, as shown in FIGS. 12 and 13, to prevent device 112 from translating axially relative to sleeve 44 in the direction shown by arrow A in FIG. 12. In some embodiments, tabs 150, 156 create a clicking sound when tabs 150, 156 to move toward one another and surfaces 150b, 156b engage surface 58 of flange 50, which indicates the device 112 is properly assembled with sleeve 44.

Figure 8:
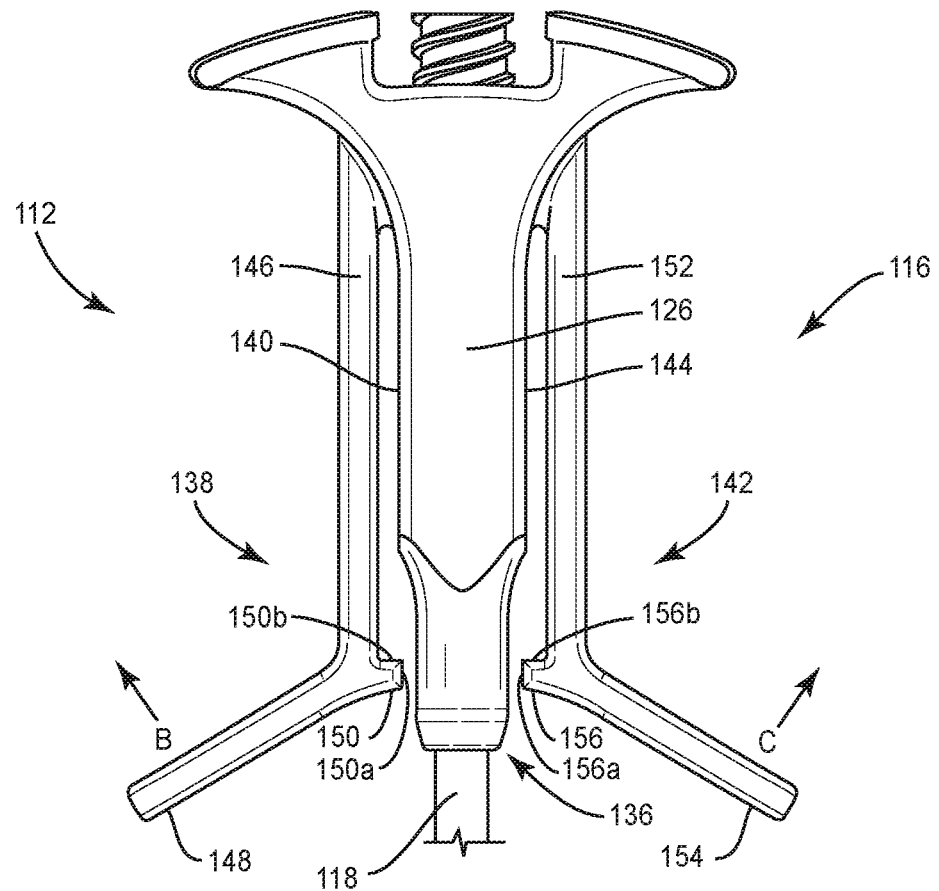
FIG. 8 is an enlarged side view of a portion of the component shown in FIG. 6.
Figure 9:
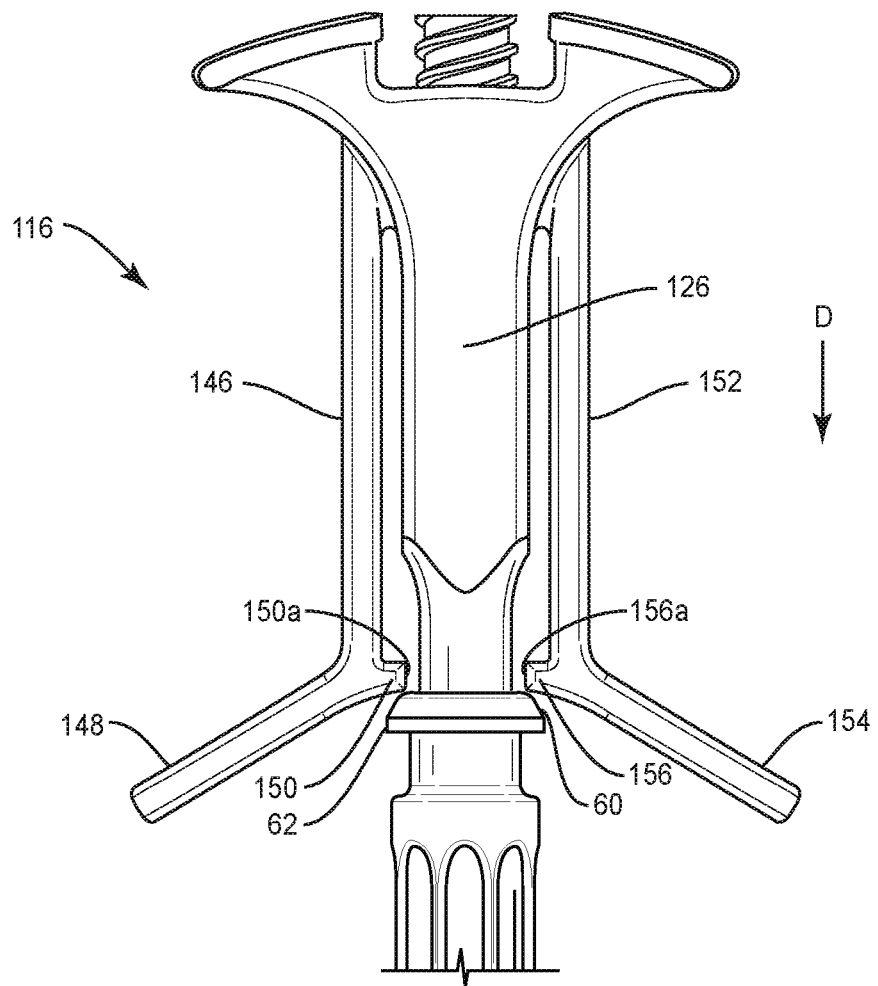
FIG. 9 is an enlarged side view of a portion of the components of the surgical system shown in FIG. 1, with the components in an unassembled configuration.
Figure 10:
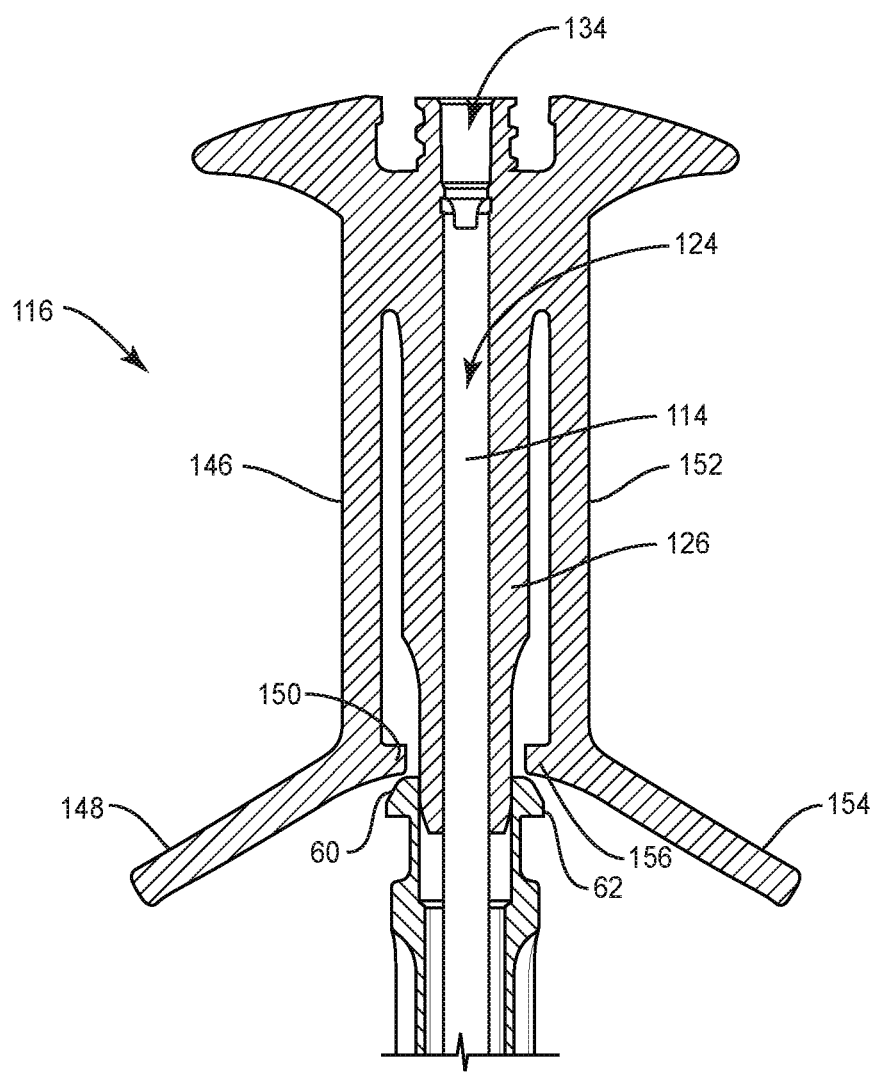
FIG. 10 an enlarged, cross sectional side view of a portion of components of the surgical system shown in FIG. 1, with the components in an unassembled configuration.

To remove device 112 from sleeve 44, a force is applied to gripping portion 148 to move gripping portion 148 relative to body 126 in the direction shown by arrow B in FIG. 8 and a force is applied to gripping portion 154 to move gripping portion 154 relative to body 126 in the direction shown by arrow C in FIG. 8 such that surface 150a is spaced the second distance apart from surface 156a. Device 112 is translated axially relative to sleeve 44 in the direction shown by arrow A in FIG. 12 such that surfaces 150a, 156a slide along surface 62. Device 112 may be translated axially relative to sleeve 44 in the direction shown by arrow A in FIG. 12 until shaft 114 is removed from channel 68.

In assembly, operation and use, driver 32 is connected with fastener 80 as discussed herein. Access to the surgical site is obtained and the particular surgical procedure is performed. The components of delivery system 30 are employed to augment the surgical treatment. For example, fastener 80 may be inserted into bone or other tissue with driver 32, for example via clockwise or counterclockwise rotation of sleeve 44 relative to sleeve 34. Device 112 is connected with driver 32 either before or after fastener 80 is inserted into bone or other tissue.

Figure 14:
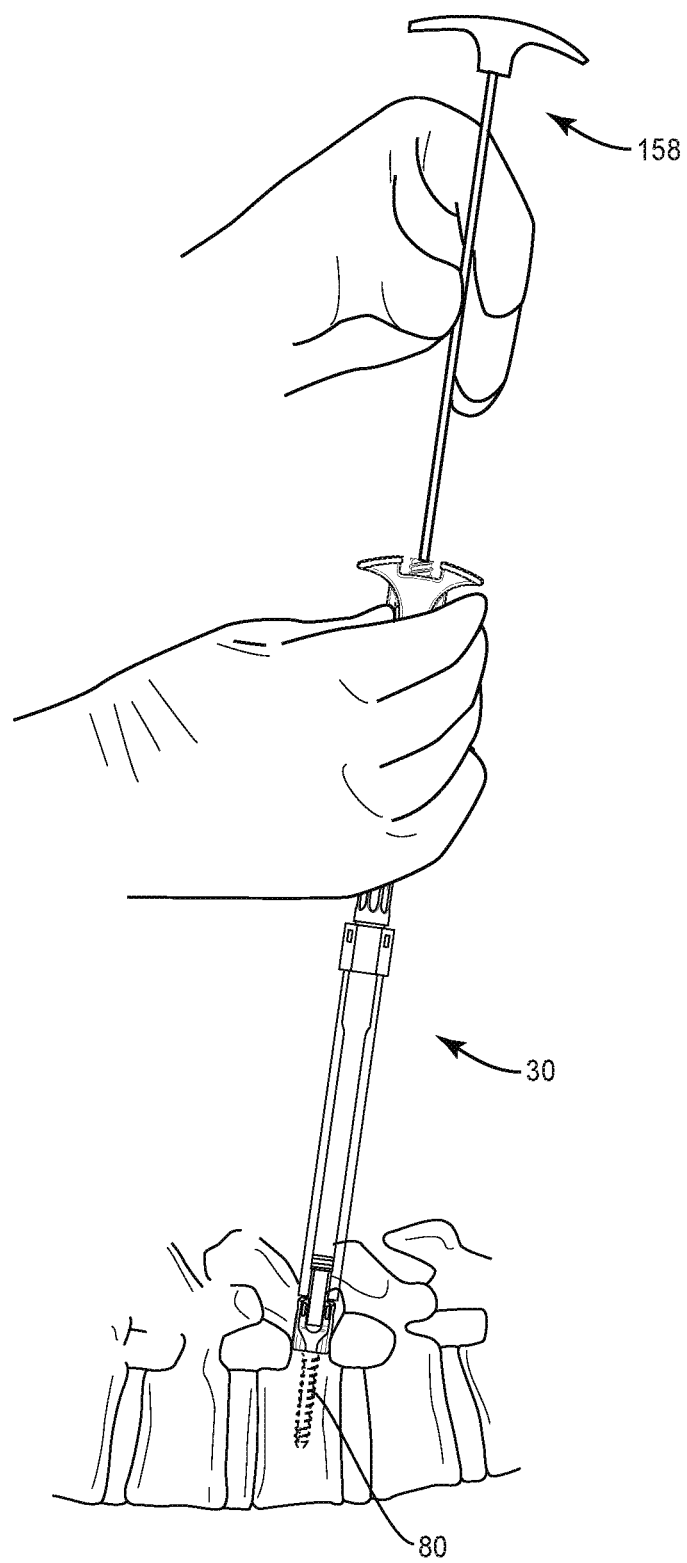
FIG. 14 is a plan view of one embodiment of the surgical system shown in FIG. 1 in accordance with the principles of the present disclosure.
Figure 15:
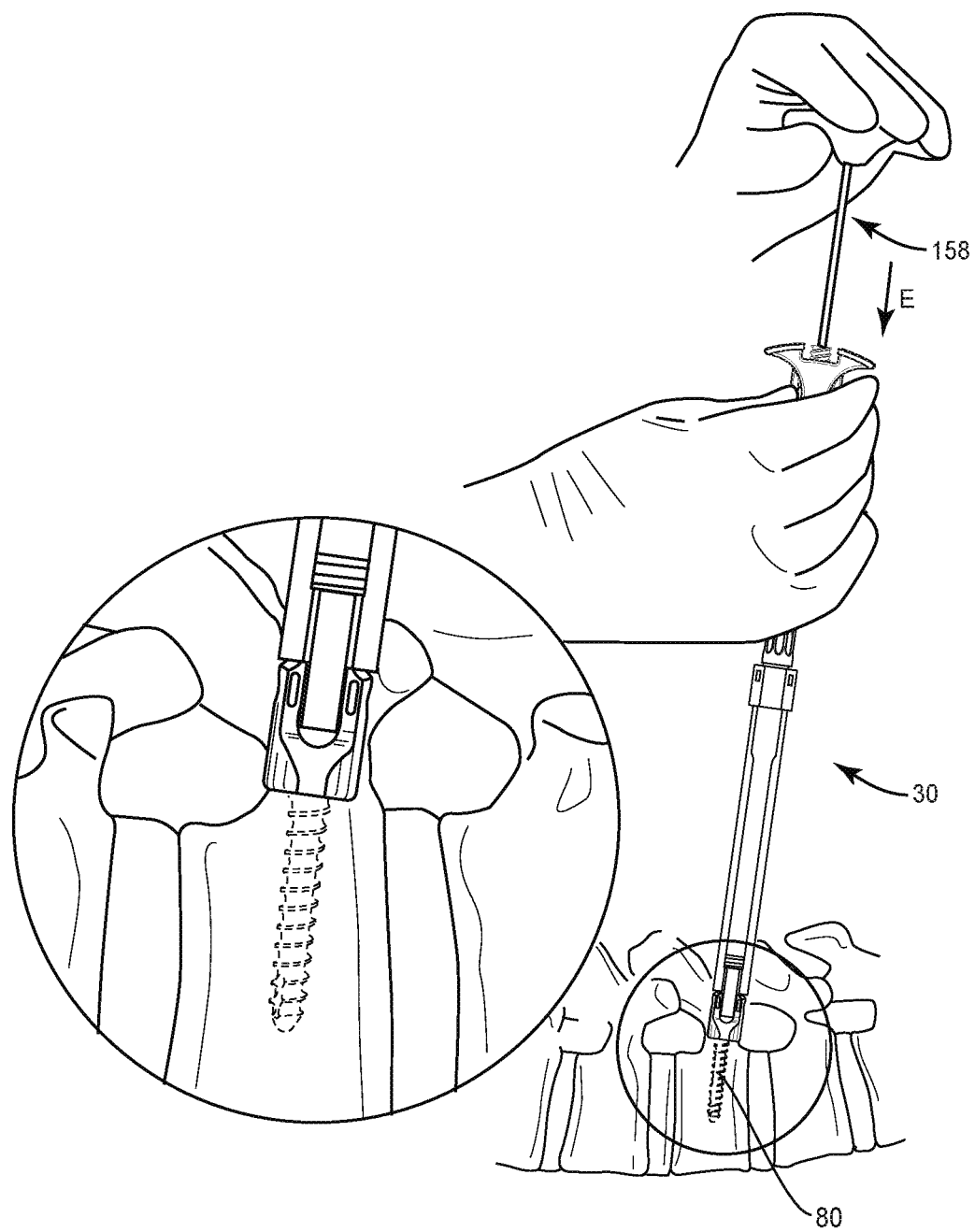
FIG. 15 is a plan view of one embodiment of the surgical system shown in FIG. 1 in accordance with the principles of the present disclosure.

In one embodiment, shown in FIGS. 14 and 15, bone filler material, such as, for example, bone cement is inserted through opening 134 and into lumen 124. The bone filler material may be inserted into lumen 124 before or after device 112 is connected with driver 32. A plunger 158 is aligned with opening 134, as shown in FIG. 14. Plunger 158 is then translated relative to handle 116 in the direction shown by arrow E in FIG. 15 such that plunger 158 pushes the bone filler material through lumen 124 and bores 78, 106 and the bone filler material exits screw 86 via one or more openings in screw 86. As the bone filler material cures, it will bond screw 86 with bone or other tissue. Upon completion of a surgical procedure, plunger 158 may be removed from device 112, and driver 32 is removed from the surgical site. In some embodiments, device 112 is disengaged from driver 32 either before or after driver 32 is removed from the surgical site. In some embodiments, a spinal construct, such as, for example, a spinal rod is inserted into implant cavity 92 after driver 32 is removed from the surgical site and a setscrew is engaged with receiver 84 such that threads on an outer surface of the setscrew engage the threads on the inner surfaces of arms 88, 90. The setscrew is rotated relative to receiver 84 until the setscrew engages the rod to fix the rod relative to receiver 84.

Figure 16:
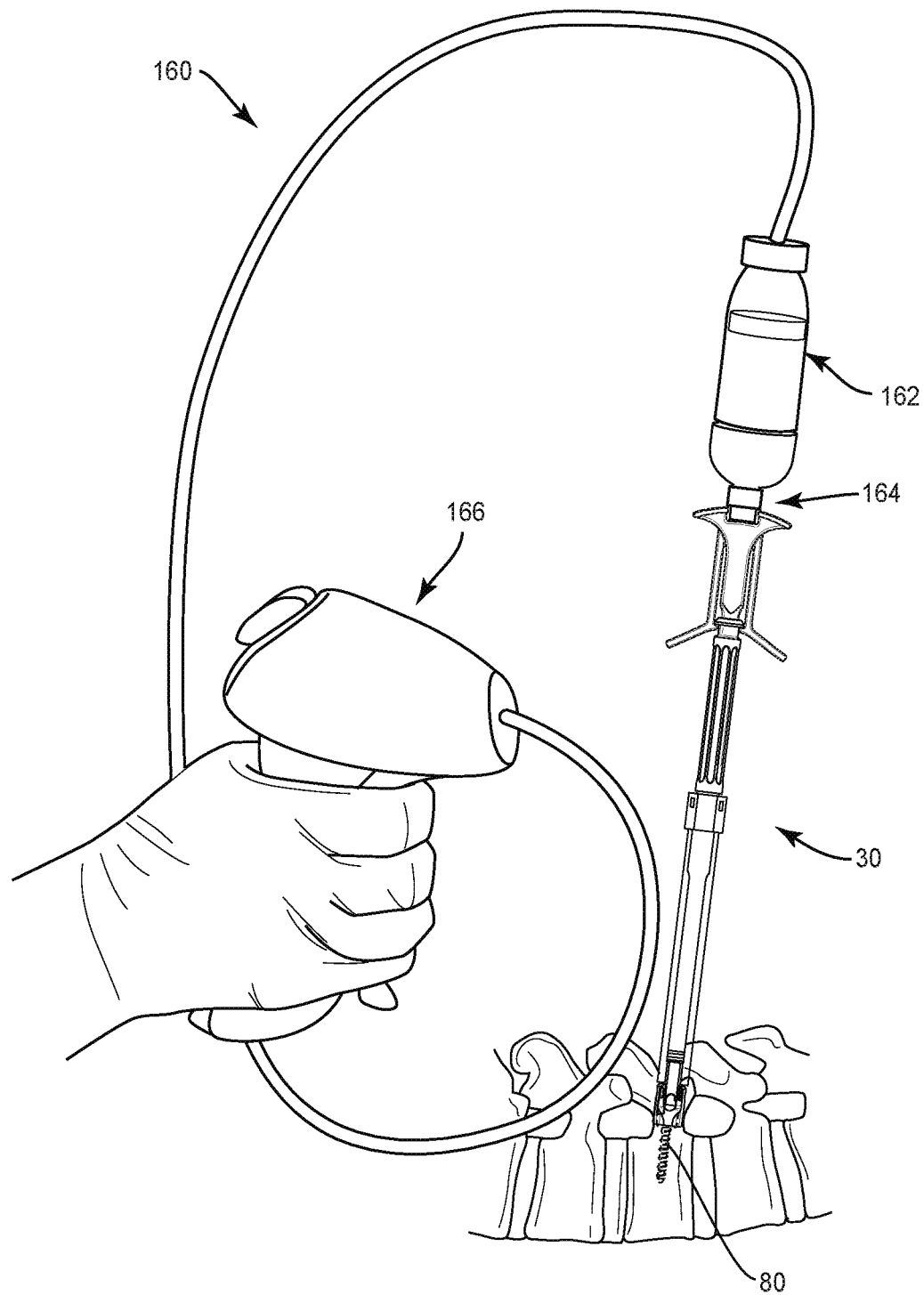
FIG. 16 is a plan view of one embodiment of the surgical system shown in FIG. 1 in accordance with the principles of the present disclosure.

In one embodiment, shown in FIG. 16, delivery system 30 includes a cement delivery system 160 having a cartridge 162 that is connected to handle 112 by a luer lock 164 and a cement delivery gun 166 that is connected to cartridge 162. Threads of luer lock 164 are mated with threads of surface 130 to connect cartridge 162 to handle 112. Cartridge 162 is loaded with a bone filler material, such as, for example, bone cement either before or after cartridge 162 is connected to handle 112. An actuator, such as, for example, a trigger handle of cement delivery gun 166 is activated to move the bone filler material through lumen 124 and bores 78, 106 such that the bone filler material exits screw 86 via one or more openings in screw 86. Engagement of surfaces 150b, 156b prevents device 112 from translating axially relative to sleeve 44 in the direction shown by arrow A in FIG. 12 due to back pressure generated by cement delivery gun 166. As the bone filler material cures, it will bond screw 86 with bone or other tissue. Upon completion of a surgical procedure, cement delivery system 160 may be removed from device 112, and driver 32 is removed from the surgical site. In some embodiments, device 112 is disengaged and/or disconnected from driver 32 either before or after driver 32 is removed from the surgical site. In some embodiments, a spinal construct, such as, for example, a spinal rod is inserted into implant cavity 92 after driver 32 is removed from the surgical site and a setscrew is engaged with receiver 84 such that threads on an outer surface of the setscrew engage the threads on the inner surfaces of arms 88, 90. The setscrew is rotated relative to receiver 84 until the setscrew engages the rod to fix the rod relative to receiver 84.

Delivery system 30 can include one or a plurality of bone fasteners such as those described herein and/or fixation elements, which may be employed with a single vertebral level or a plurality of vertebral levels. In some embodiments, the bone fasteners may be engaged with vertebrae in various orientations, such as, for example, series, parallel, offset, staggered and/or alternate vertebral levels. In some embodiments, the bone fasteners and/or fixation elements may include one or a plurality of multi-axial screws, sagittal angulation screws, pedicle screws, mono-axial screws, uni-planar screws, fixed screws, tissue penetrating screws, conventional screws, expanding screws, wedges, anchors, buttons, clips, snaps, friction fittings, compressive fittings, expanding rivets, staples, nails, adhesives, posts, fixation plates and/or posts. In some embodiments, system 30 may comprise various instruments including the configuration of the present disclosure, such as, for example, inserters, extenders, reducers, spreaders, distractors, blades, retractors, clamps, forceps, elevators and drills, which may be alternately sized and dimensioned, and arranged as a kit, according to the requirements of a particular application.

In some embodiments, delivery system 30 includes an agent, which may be disposed, packed, coated or layered within, on or about the components and/or surfaces of delivery system 30. In some embodiments, the agent may include bone growth promoting material, such as, for example, bone graft to enhance fixation of the fixation elements with vertebrae. The components of delivery system 30 can be made of radiolucent materials such as polymers. Radiomarkers may be included for identification under x-ray, fluoroscopy, CT or other imaging techniques. In some embodiments, the agent may include one or a plurality of therapeutic agents and/or pharmacological agents for release, including sustained release, to treat, for example, pain, inflammation and degeneration.

In one embodiment, shown in FIGS. 17-21, delivery system 30 includes a driver 168 that is similar to driver 32. Driver 168 includes an outer sleeve 170 having a lower portion 172 and an upper portion 174 that is connected with lower portion 172. Lower portion 172 extends along a longitudinal axis L3 between an end 176 and an opposite end 178. End 176 includes a circumferential cutout 180 configured for disposal of an end 182 of upper portion 174 to connect upper portion 174 with lower portion 172. In some embodiments, upper portion 174 is connected with lower portion 172 to provisionally fix upper portion 174 relative to lower portion 172 such that rotation of upper portion 174 about axis L3 also rotates lower portion 172 about axis L3. In some embodiments, upper portion 174 can be variously connected with lower portion 172, such as, for example, monolithic, integral connection, frictional engagement, threaded engagement, mutual grooves, screws, adhesive, nails, barbs and/or raised element. End 178 includes a tip 184 defining a drive portion configured for engagement with an implant, such as, for example, bone fastener 80, as discussed herein. In some embodiments, the drive portion may include a square, triangular, polygonal, star or hexalobe cross sectional configuration configured engage a correspondingly shaped portion tool engaging portion 102 of fastener 80.

Figure 20:
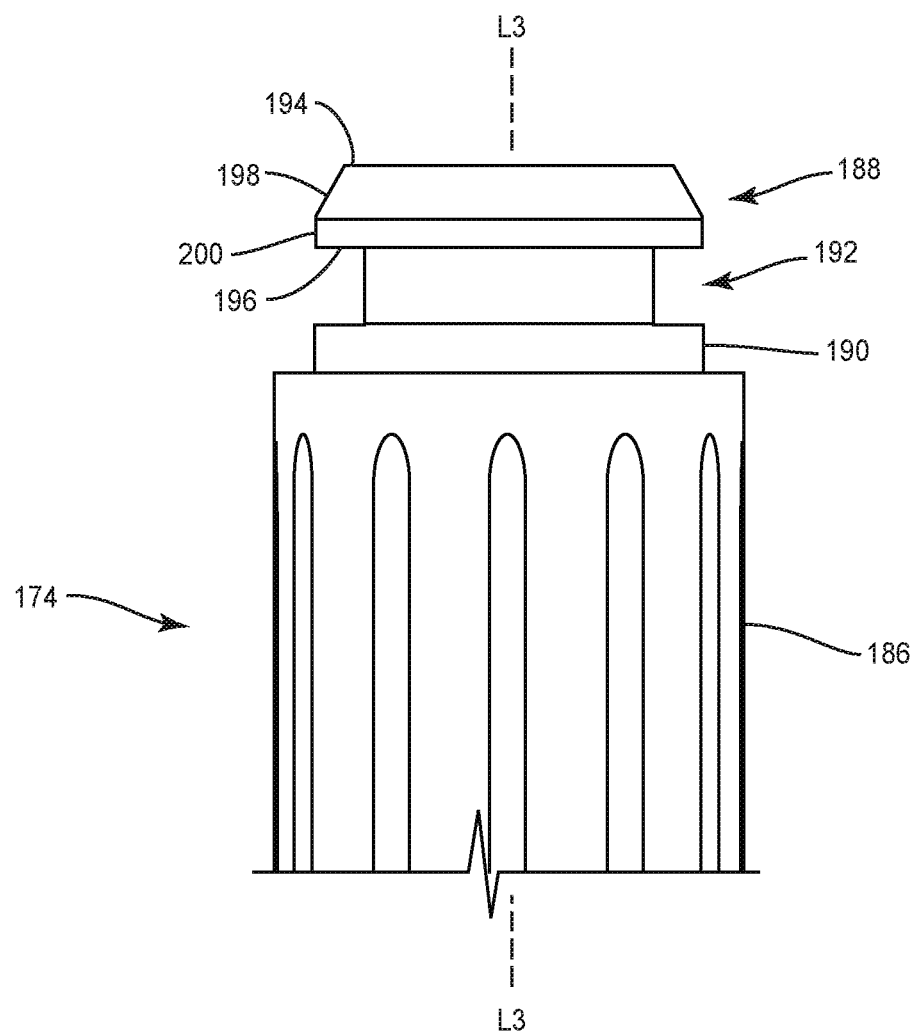
FIG. 20 is an enlarged side view of a portion of the component shown in FIG. 18.
Figure 21:
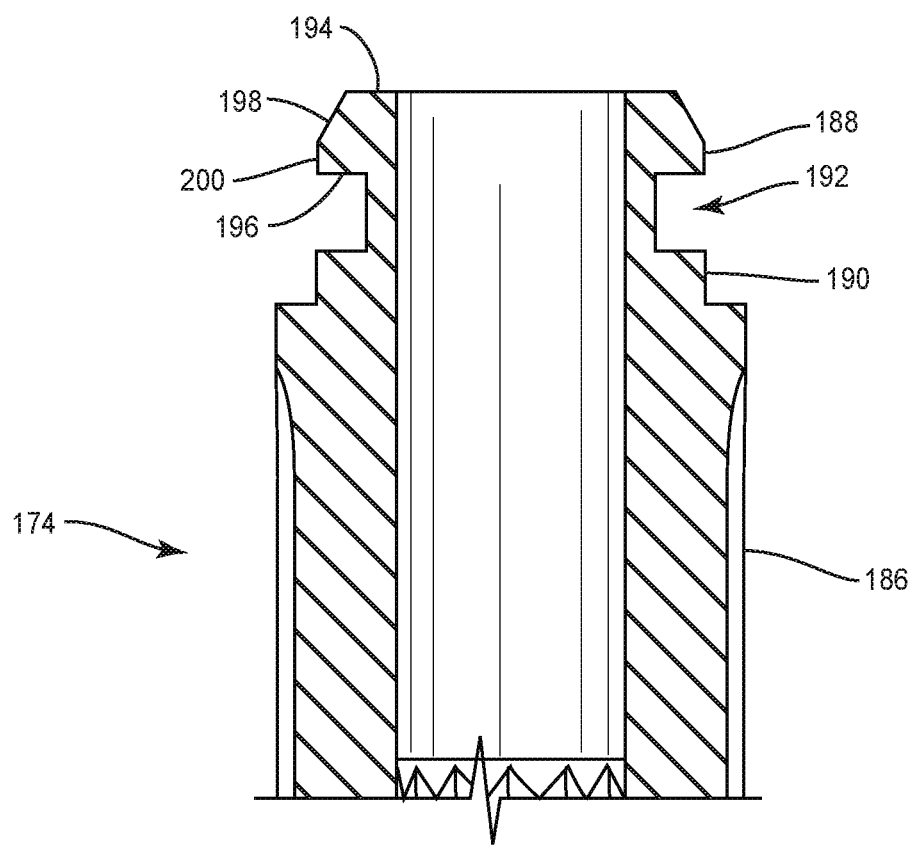
FIG. 21 is an enlarged, cross sectional side view of a portion of the component shown in FIG. 18.

Upper portion 174 includes an end 186 opposite end 182. End 186 includes a first mating element, such as, for example, a flange 188 that is similar to flange 50. Flange 188 is spaced apart from a flange 190 by an undercut, such as, for example, a recess 192. Flange 188 includes opposite surfaces 194, 196 that each extend perpendicular to axis L3 and surfaces 198, 200 that are each positioned between surfaces 194, 196, as best shown in FIGS. 20 and 21. Surface 194 defines an end surface of end 186. Surface 198 extends transverse to axis L3 and surface 200 extends parallel to axis L3.

Lower portion 172 includes an inner surface 202 defining a passageway 204 and upper portion 174 includes an inner surface 206 defining a channel 208 that is in communication and coaxial with passageway 204. Passageway 204 and channel 208 are configured for disposal of an inner sleeve 210 such that sleeve 210 is rotatable relative to sleeve 170 about axis L3. Sleeve 210 includes an end 212 and an opposite end 214 having a threaded outer surface 228. A distal portion of end 212 is positioned in passageway 204 and a proximal portion 216 of end 212 is positioned in channel 208. Proximal portion 216 includes an inner surface 218 defining a socket 220. In some embodiments, socket 220 may include a square, triangular, polygonal, star or hexalobe cross sectional configuration configured engage a correspondingly shaped portion of a thumbwheel 222, as discussed herein.

Upper portion 174 includes a window 224 that is configured to allow visualization of a portion of device 112 and a window 226 that is configured to allow grasping of thumbwheel 222. Thumbwheel 222 includes a bit (not shown) disposed in socket 220. The bit has a shape that corresponds to the shape of socket 220 such that rotation of thumbwheel 222 relative to sleeve 170 about axis L3 also rotates sleeve 210 relative to sleeve 170 about axis L3.

To connect driver 168 with fastener 80, thumbwheel 222 is rotated relative to sleeve 170 about axis L3 in a first rotational direction, such as, for example clockwise or counterclockwise. Rotation of thumbwheel 222 relative to sleeve 170 about axis L3 in the first rotational direction causes rotation of sleeve 210 relative to sleeve 170 about axis L3 in the first rotational direction. As sleeve 210 rotates relative to sleeve 170 about axis L3 in the first rotational direction, the threads on surface 228 of sleeve 210 mate with the threads on the inner surfaces of arms 88, 90 of fastener 80. Further rotation of sleeve 210 relative to sleeve 170 about axis L3 in the first rotational direction causes sleeve 210 to translate axially relative to sleeve 170 in the direction shown by arrow F in FIG. 19. As sleeve 210 translates axially relative to sleeve 170 in the direction shown by arrow F in FIG. 19, tip 184 is inserted into tool engaging portion 102 of screw 86. Simultaneous engagement of tip 184 with tool engaging portion 102 and the threads on surface 228 of sleeve 210 with the threads on the inner surfaces of arms 88, 90 of fastener 80 prevents screw 86 from pivoting relative to receiver 84.

To remove driver 168 from fastener 80, thumbwheel 222 is rotated relative to sleeve 170 about axis L3 in an opposite second rotational direction, such as, for example clockwise or counterclockwise. Rotation of thumbwheel 222 relative to sleeve 170 about axis L3 in the second rotational direction causes rotation of sleeve 210 relative to sleeve 170 about axis L3 in the second rotational direction. As sleeve 210 rotates relative to sleeve 170 about axis L3 in the second rotational direction, sleeve 210 translates axially relative to sleeve 170 in the direction shown by arrow G in FIG. 19. As sleeve 210 translates axially relative to sleeve 170 in the direction shown by arrow G in FIG. 19, tip 184 moves out of tool engaging portion 102 of screw 86 and the threads on surface 228 of sleeve 210 disengage the threads on the inner surfaces of arms 88, 90 of fastener 80, at which point driver 168 can be fully removed from fastener 80.

In assembly, operation and use, driver 168 is connected with fastener 80 as discussed herein. Access to the surgical site is obtained and the particular surgical procedure is performed. The components of delivery system 30 are employed to augment the surgical treatment. For example, fastener 80 may be inserted into bone or other tissue with driver 168, for example via clockwise or counterclockwise rotation of sleeve 170.

Figure 17:
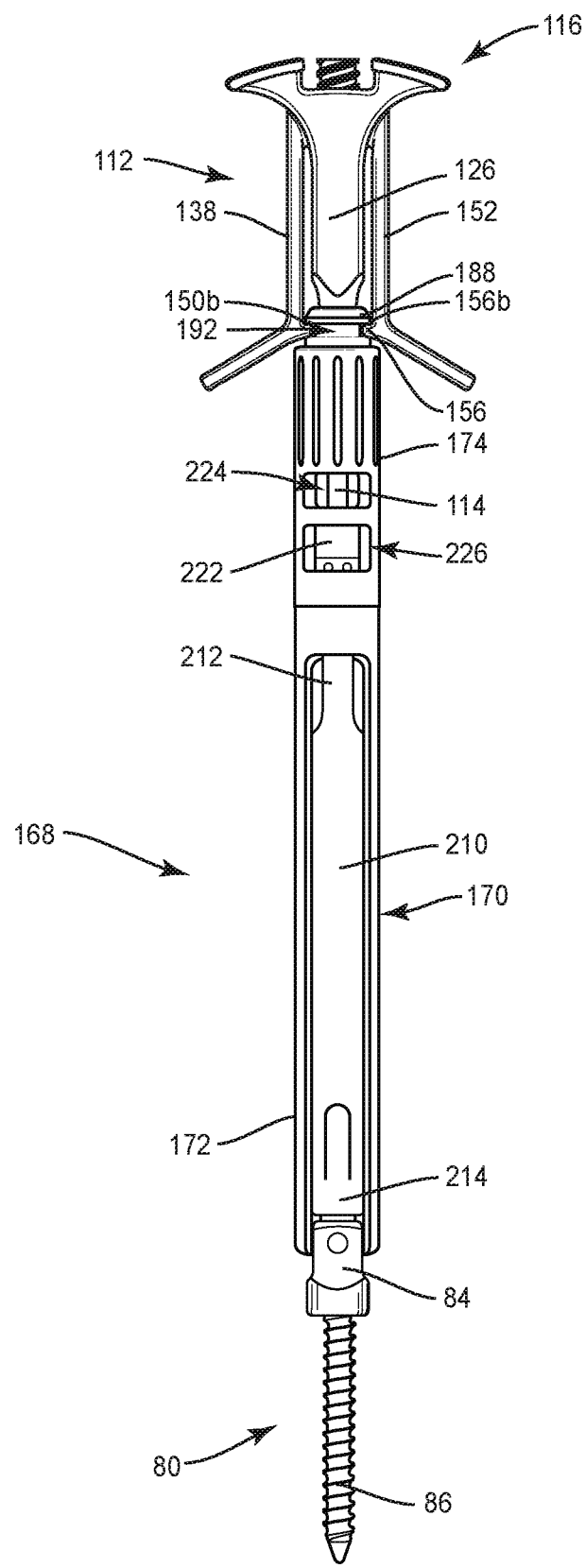
FIG. 17 is a side view of components of one embodiment of a surgical system in accordance with the principles of the present disclosure.

Device 112 is connected with driver 168 either before or after fastener 80 is inserted into bone or other tissue. To connect device 112 with driver 168, shaft 114 is inserted into channel 208 such that axis L3 is coaxial with axis L1. Device 112 is then translated axially relative to sleeve 170 in the direction shown by arrow F in FIG. 19 until shaft 114 extends through thumbwheel 222 and conical portion 136 is positioned within channel 208. As device 112 translates axially relative to sleeve 170 in the direction shown by arrow F in FIG. 19, surface 150*a* of tab 150 slides along surface 198 of flange 188 and surface 156*a* of tab 156 slides along surface 198. As surfaces 150*a*, 156*a* slide along surface 198, wings 138, 142 deflect outwardly from body 126 such that the distance between surfaces 150*a*, 156*a* increase from the first distance to the second distance. Device 112 is further translated axially relative to sleeve 170 in the direction shown by arrow F in FIG. 19 when surfaces 150*a*, 156*a* are spaced apart by the second distance such that surfaces 150*a*, 156*a* slide along surface 200 of flange 188. Device 112 is further translated axially relative to sleeve 170 in the direction shown by arrow F in FIG. 19 such that tabs 150, 156 are aligned with recess 198. The inward bias of wings 138, 142 causes tabs 150, 156 to move toward one another such that surface 150*a* is spaced the first distance apart from surface 156*a* and surfaces 150*b*, 156*b* engage surface 196 of flange 188, as shown in FIG. 17 to prevent device 112 from translating axially relative to sleeve 170 in the direction shown by arrow G in FIG. 19. In some embodiments, tabs 150, 156 create a clicking sound when tabs 150, 156 to move toward one another and surfaces 150*b*, 156*b* engage surface 196 of flange 188, which indicates the device 112 is properly assembled with sleeve 170.

In one embodiment, bone filler material, such as, for example, bone cement is inserted through opening 134 and into lumen 124. The bone filler material may be inserted into lumen 124 after device 112 is connected with driver 168. Plunger 158 is aligned with opening 134. Plunger 158 is then translated relative to handle 116 in the direction shown by arrow F in FIG. 19 such that plunger 158 pushes the bone filler material through lumen 124, an aperture 230 that extends through tip 184 and bore 106 such that the bone filler material exits screw 86 via one or more openings in screw 86. As the bone filler material cures, it will bond screw 86 with bone or other tissue. Upon completion of a surgical procedure, plunger 158 may be removed from device 112, and driver 168 is removed from the surgical site. In some embodiments, device 112 is disengaged from driver 168 either before or after driver 168 is removed from the surgical site. To remove device 112 from sleeve 170, a force is applied to gripping portion 148 to move gripping portion 148 relative to body 126 in the direction shown by arrow B in FIG. 8 and a force is applied to gripping portion 154 to move gripping portion 154 relative to body 126 in the direction shown by arrow C in FIG. 8 such that surface 150*a* is spaced the second distance apart from surface 156*a*. Device 112 is translated axially relative to sleeve 170 in the direction shown by arrow F in FIG. 19 such that surfaces 150*a*, 156*a* slide along surface 200. Device 112 may be translated axially relative to sleeve 170 in the direction shown by arrow F in FIG. 19 until shaft 114 is removed from channel 208. In some embodiments, a spinal construct, such as, for example, a spinal rod is inserted into implant cavity 92 after driver 168 is removed from the surgical site and a setscrew is engaged with receiver 84 such that threads on an outer surface of the setscrew engage the threads on the inner surfaces of arms 88, 90. The setscrew is rotated relative to receiver 84 until the setscrew engages the rod such that the rod is fixed relative to receiver 84.

In one embodiment, threads of luer lock 164 are mated with threads of surface 130 to connect cartridge 162 to handle 112. Cartridge 162 is loaded with a bone filler material, such as, for example, bone cement either before or after cartridge 162 is connected to handle 112. The trigger handle of cement delivery gun 166 is activated to move the bone filler material through lumen 124, aperture 230 and bore 106 such that the bone filler material exits screw 86 via one or more openings in screw 86. As the bone filler material cures, it will bond screw 86 with bone or other tissue. Upon completion of a surgical procedure, cement delivery system 160 may be removed from device 112, and driver 168 is removed from the surgical site. In some embodiments, device 112 is disengaged from driver 168 either before or after driver 168 is removed from the surgical site. In some embodiments, a spinal construct, such as, for example, a spinal rod is inserted into implant cavity 92 after driver 168 is removed from the surgical site and a setscrew is engaged with receiver 84 such that threads on an outer surface of the setscrew engage the threads on the inner surfaces of arms 88, 90. The setscrew is rotated relative to receiver 84 until the setscrew engages the rod such that the rod is fixed relative to receiver 84.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A delivery system comprising:
an implant;
a first instrument comprising an outer sleeve defining a passageway, the first instrument comprising an inner sleeve having a first end disposed in the passageway and a second end including a first mating element, the inner sleeve defining a channel, the first end defining an opening in communication with the channel, the first instrument comprising a tip removably connected with the inner sleeve, the tip having a flange positioned in the channel, the flange having a diameter greater than a diameter of the opening, the tip comprising a threaded outer surface configured to engage threads of the implant to connect the first instrument to the implant, the tip comprising a drive portion configured for disposal in a socket of the implant; and
a second instrument comprising a hollow shaft defining a longitudinal axis, the shaft being disposed in the channel, the second instrument comprising a handle coupled to the shaft, the handle comprising a body and a second mating element extending from the body of the handle, the second mating element being configured to engage the first mating element to secure the second instrument to the first instrument,
wherein the tip is configured to rotate relative to the implant about the longitudinal axis when the first instrument is connected to the implant and the second instrument is secured to the first instrument.

2. A delivery system as recited in claim 1, wherein engagement of the mating elements prevents the second instrument from translating proximally relative to the first instrument.

3. A delivery system as recited in claim 1, wherein the first mating element is a flange extending outwardly from an outer surface of the inner sleeve.

4. A delivery system as recited in claim 3, wherein the second mating element comprises a wing extending from the body of the handle in a cantilevered configuration.

5. A delivery system as recited in claim 3, wherein the second mating element comprises a first wing extending from a first side the body of the handle in a cantilevered configuration and a second wing extending from an opposite second side of the body of the handle in a cantilevered configuration.

6. A delivery system as recited in claim 5, wherein:
the first wing comprises an extension extending from the first side and a tab extending from the extension;
the second wing comprises an extension extending from the second side and a tab extending from the extension of the second wing;
the extensions each extend parallel to the longitudinal axis and end surfaces of the tabs each extend parallel to the longitudinal axis; and
the tabs engage the flange of the inner sleeve to secure the second instrument to the first instrument.

7. A delivery system as recited in claim 6, wherein the end surfaces of the tabs face one another.

8. A delivery system as recited in claim 5, wherein:
the flange of the inner sleeve is a first flange, the inner sleeve comprising a second flange and a recess between the first flange and the second flange;
the first wing comprises an extension extending from the first side and a tab extending from the extension;
the second wing comprises an extension extending from the second side and a tab extending from the extension of the second wing; and
the extensions each extend parallel to the longitudinal axis and end surfaces of the tabs are each positioned in the recess and extend parallel to the longitudinal axis.

9. A delivery system as recited in claim 1, wherein the body of the handle includes a cylindrical portion coaxial with the shaft, the cylindrical portion having a threaded outer surface and an inner surface defining an opening in communication and coaxial with a lumen of the shaft.

10. A delivery system as recited in claim 1, wherein the tip comprises a bore in communication and coaxial with the channel.

11. A delivery system as recited in claim 1, wherein the first end is rotatably disposed in the passageway.

12. A delivery system comprising:
an implant comprising a threaded screw and a head coupled to the screw, the screw comprising a bore extending through opposite ends of the screw, the head having a threaded inner surface;
a first instrument comprising an outer sleeve defining a passageway, the outer sleeve being coupled directly to the head, the first instrument comprising an inner sleeve having a first end rotatably disposed in the passageway and a second end including a first mating element, the inner sleeve defining a channel, the first end defining an opening in communication with the channel, the first instrument comprising a tip removably connected with the inner sleeve, the tip having a threaded outer surface engaging the threaded inner surface to couple the tip to the head, the tip comprising a flange positioned in the channel, the flange having a diameter greater than a diameter of the opening, the tip comprising a drive portion positioned in the bore; and
a second instrument comprising a hollow shaft defining a longitudinal axis, the shaft being disposed in the channel, the second instrument comprising a handle coupled to the shaft, the handle comprising a body and a second mating element extending from the body of the handle,
wherein the second mating element engages the first mating element to secure the second instrument to the first instrument such that the second instrument is prevented from translating proximally relative to the first instrument, and
wherein the tip is configured to rotate relative to the head about the longitudinal axis when the outer sleeve is coupled to the head and the second instrument is secured to the first instrument.

13. A delivery system as recited in claim 12, wherein the bore is in communication and coaxial with the channel.

14. A delivery system as recited in claim 12, wherein the first mating element is a flange extending outwardly from an outer surface of the inner sleeve.

15. A delivery system as recited in claim 14, wherein the second mating element comprises a first wing extending from a first side the body of the handle in a cantilevered configuration and a second wing extending from an opposite second side of the body of the handle in a cantilevered configuration.

16. A delivery system as recited in claim 15, wherein:
the first wing comprises an extension extending from the first side and a tab extending from the extension;
the second wing comprises an extension extending from the second side and a tab extending from the extension of the second wing;
the extensions each extend parallel to the longitudinal axis and the tabs each extend perpendicular to the longitudinal axis such that end surfaces of the tabs each extend parallel to the longitudinal axis; and
the tabs engage the flange of the inner sleeve to secure the second instrument to the first instrument.

17. A delivery system as recited in claim 16, wherein the end surfaces of the tabs face one another.

18. A delivery system as recited in claim 12, wherein the body of the handle includes a cylindrical portion coaxial with the shaft, the cylindrical portion having a threaded outer surface and an inner surface defining an opening in communication and coaxial with a lumen of the shaft.

19. A delivery system as recited in claim 18, further comprising an injector coupled to the cylindrical portion, the injector comprising bone cement therein, the injector being configured to deliver the bone cement through the opening and the lumen and into the bore.

20. A delivery system comprising:
a bone fastener comprising a threaded screw and a head coupled to the screw, the screw comprising an inner surface defining a bore extending through opposite ends of the screw, the screw comprising an opening extending through the inner surface and an opposite outer surface of the screw, the head having a threaded inner surface;
a driver comprising an outer sleeve defining a passageway, the outer sleeve being coupled directly to the head, the driver comprising an inner sleeve having a first end rotatably disposed in the passageway and a second end including a flange, the inner sleeve defining a channel, the first end defining an opening in communication with the channel, the driver comprising a tip removably connected with the inner sleeve, the tip comprising a flange positioned in the channel, the flange of the tip having a diameter greater than a diameter of the opening defined by the inner sleeve, the tip having a threaded outer surface engaging the threaded inner surface to couple the tip to the head, the tip comprising a drive portion positioned in the bore; and a bone filler device comprising a hollow shaft defining a longitudinal axis, the shaft being disposed in the channel, the bone filler device comprising a handle coupled to the shaft, the handle comprising a body including a cylindrical portion coaxial with the shaft, the cylindrical portion having a threaded outer surface and an inner surface defining an opening in communication and coaxial with a lumen of the shaft, the handle comprising a first wing extending from a first side the body of the handle in a cantilevered configuration and a second wing extending from an opposite second side of the body of the handle in a cantilevered configuration, the first wing comprising an extension extending from the first side and a tab extending from the extension, the second wing comprising an extension extending from the second side and a tab extending from the extension of the second wing, the extensions each extending parallel to the longitudinal axis and the tabs each extending perpendicular to the longitudinal axis, wherein the tabs engage the flange of the second end to secure the bone filler device to the driver such that the bone filler device is prevented from translating proximally relative to the driver; and an injector coupled to the handle, the injector comprising bone cement therein, the injector being configured to deliver the bone cement through the channel and into the bore, wherein the tip is configured to rotate relative to the head about the longitudinal axis when the outer sleeve is coupled to the head and the bone filler device is secured to the driver.

* * * * *